United States Patent
Fraasch et al.

(10) Patent No.: US 12,076,073 B2
(45) Date of Patent: Sep. 3, 2024

(54) METHOD OF CONFIRMING SAFE DELIVERY PATHWAY TO PATIENT PRIOR TO ENERGY DELIVERY

(71) Applicant: Medtronic, Inc., Minneapolis, MN (US)

(72) Inventors: Steven J. Fraasch, Maple Grove, MN (US); Catherine R. Condie, Shoreview, MN (US); Trenton J. Rehberger, Minneapolis, MN (US); Mark T. Stewart, Lino Lakes, MN (US); Qin Zhang, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 415 days.

(21) Appl. No.: 16/725,020

(22) Filed: Dec. 23, 2019

(65) Prior Publication Data
US 2020/0121382 A1   Apr. 23, 2020

Related U.S. Application Data

(62) Division of application No. 15/432,134, filed on Feb. 14, 2017, now Pat. No. 10,555,768.

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1206* (2013.01); *A61B 18/1492* (2013.01);
(Continued)

(58) Field of Classification Search
CPC ............ A61B 18/1233; A61B 18/1206; A61B 18/1492; A61B 2018/00357;
(Continued)

(56) References Cited

U.S. PATENT DOCUMENTS 4,416,276 A   11/1983   Newton et al.
5,231,987 A   8/1993   Robson
(Continued)

FOREIGN PATENT DOCUMENTS

EP   2301462 A1   3/2011
EP   2912481 A1   9/2015
(Continued)

OTHER PUBLICATIONS

IEC 60601-1—Medical electrical equipment—Part 1: General requirements for basic safety and essential performance, International Electrotechnical Commission, 3rd Edition, 2005, Geneva, Switzerland.
(Continued)

*Primary Examiner* — Eun Hwa Kim
*Assistant Examiner* — Catherine C. Premraj
(74) *Attorney, Agent, or Firm* — Michael Best & Friedrich LLP

(57) ABSTRACT

Systems and methods to confirm safe delivery of treatment energy to a patient by identifying a presence of a fault in an energy delivery pathway and identifying a location of the fault within the device. The system includes a processing unit configured to calculate blood impedances external to the device based on known impedance characteristics of the device, and then to calculate impedances within the device during energy delivery based on the calculated blood impedances. The processing unit prevents the delivery of energy in an energy delivery pathway that is determined to be compromised. The processing unit is also configured to compare times for two different frequencies to travel a predetermined distance, the difference in the times corresponding to a location of a fault within the energy delivery pathway.

20 Claims, 14 Drawing Sheets

(51) Int. Cl.
  *A61B 18/00* (2006.01)
  *A61B 18/16* (2006.01)
  *A61N 1/08* (2006.01)

(52) U.S. Cl.
  CPC .............. *A61B 2018/00357* (2013.01); *A61B 2018/00398* (2013.01); *A61B 2018/00577* (2013.01); *A61B 2018/00666* (2013.01); *A61B 2018/00708* (2013.01); *A61B 2018/00875* (2013.01); *A61B 2018/00898* (2013.01); *A61B 2018/1273* (2013.01); *A61B 2018/128* (2013.01); *A61B 2018/1407* (2013.01); *A61B 2018/162* (2013.01); *A61N 2001/083* (2013.01)

(58) Field of Classification Search
  CPC ........... A61B 2018/00398; A61B 2018/00577; A61B 2018/00666; A61B 2018/00708; A61B 2018/00875; A61B 2018/00898; A61B 2018/1273; A61B 2018/128; A61B 2018/1407; A61B 2018/162; A61N 2001/083
  See application file for complete search history.

(56) References Cited

U.S. PATENT DOCUMENTS

| | | | |
|---|---|---|---|
| 5,361,776 A | 11/1994 | Samuelson et al. | |
| 6,796,980 B2 | 9/2004 | Hall | |
| 7,070,595 B2 | 7/2006 | Ormsby et al. | |
| 7,966,137 B2 | 6/2011 | Fantoni | |
| 8,352,033 B2 | 1/2013 | Kroll | |
| 8,700,156 B2 | 4/2014 | Kroll | |
| 2004/0257127 A1* | 12/2004 | Levin | H03F 3/72 327/112 |
| 2008/0172050 A1* | 7/2008 | Satake | A61B 18/1492 606/33 |
| 2008/0195162 A1* | 8/2008 | Lippert | A61B 5/053 607/9 |
| 2011/0071516 A1* | 3/2011 | Gregg | 606/34 |
| 2012/0316454 A1* | 12/2012 | Carter | A61N 1/37229 600/547 |
| 2015/0005862 A1* | 1/2015 | Kroll | A61N 1/0563 607/122 |
| 2016/0310204 A1* | 10/2016 | Mchenry | A61B 18/1233 |

FOREIGN PATENT DOCUMENTS

| | | |
|---|---|---|
| KR | 101570506 B1 | 11/2015 |
| WO | 2016160448 A2 | 10/2016 |

OTHER PUBLICATIONS

International Search Report and Written Opinion dated Jun. 11, 2018, for corresponding International Application No. PCT/US2018/015862; International Filing Date: Jan. 30, 2018; consisting of 30—pages.
China National Intellectual Property Administration Second Office Action for Application No. 201880011938.X dated May 7, 2022 (7 pages including English translation).
European Patent Office Examination Report for Application No. 20206030.7 dated Mar. 11, 2024 (8 pages).

* cited by examiner

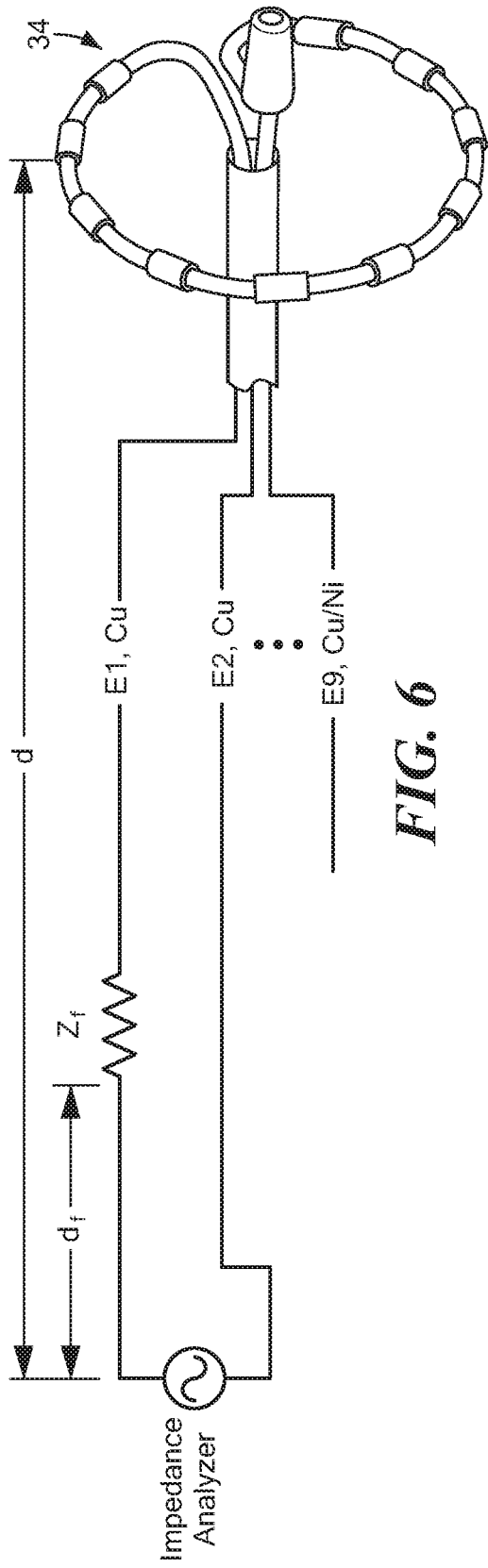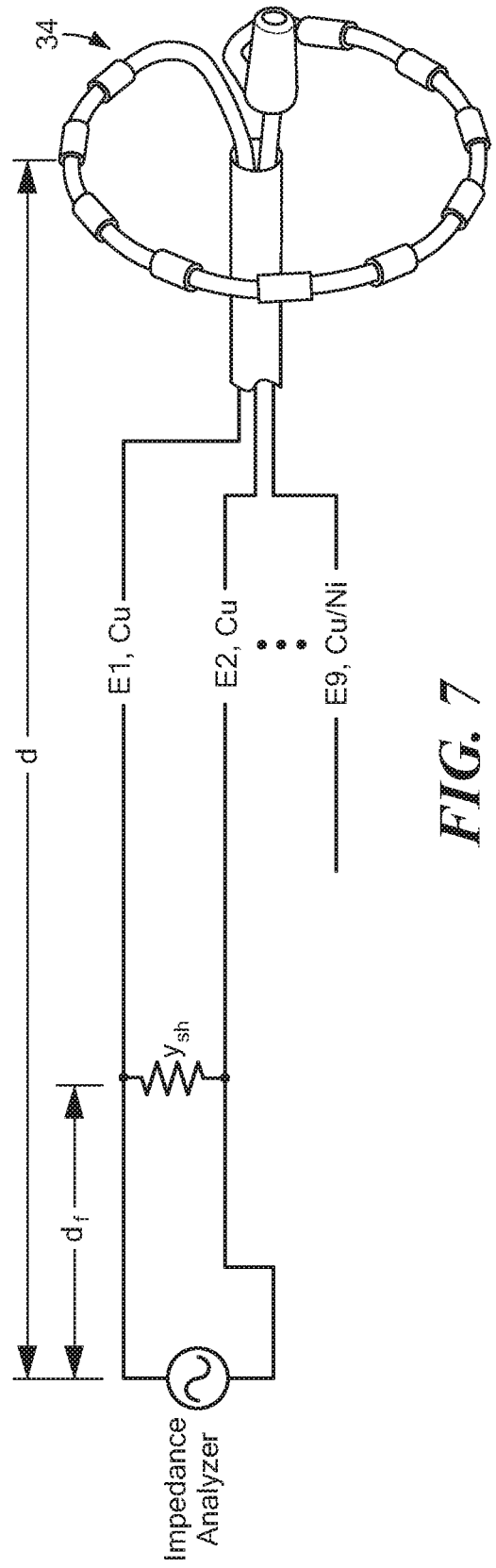

METHOD OF CONFIRMING SAFE DELIVERY PATHWAY TO PATIENT PRIOR TO ENERGY DELIVERY

CROSS-REFERENCE TO RELATED APPLICATION

This application is a divisional of U.S. Utility patent application Ser. No. 15/432,134, filed Feb. 14, 2017, entitled METHOD OF CONFIRMING SAFE DELIVERY PATHWAY TO PATIENT PRIOR TO ENERGY DELIVERY, now issued as U.S. Pat. No. 10,555,768, issued Feb. 11, 2020, the entirety of which is incorporated herein by reference.

STATEMENT REGARDING FEDERALLY SPONSORED RESEARCH OR DEVELOPMENT n/a

TECHNICAL FIELD

This disclosure relates to a method and system for confirming safe energy delivery during an ablation or treatment procedure and for identifying of a location of potential short or open circuit within an ablation or treatment device.

BACKGROUND

Cardiac arrhythmias disrupt normal heart rhythm and cardiac efficiency. These arrhythmias can be treated using, for example, pulsed field ablation (PFA) or radiofrequency (RF) ablation. The delivery of ablation therapy involves the use of a set of components that requires a reliable electrical pathway for the two-way transmission of electrical signals. These components include: an energy source in the form of pulsed or continuous wave signals such as a pulsed electric field or pulsed RF generator, an ablation delivery catheter that applies PFA or pulsed RF energy to intended endocardial locations in the heart; a catheter electrode distribution system (CEDS); and a set of interconnecting cables.

The CEDS performs the signal adjudication task similar to that of a centralized telephone system in that it prevents mutual interference due to the co-mingling of high energy ablation and very low-energy patient-borne signals. In the downstream case, ablation energy is intended to travel from equipment to the patient, whereas signals that originate at the intracardiac catheter electrodes travel to operating room monitoring equipment in the upstream case. These upstream signals include contact sensing and lesion assessment impedance, navigation, electrode thermocouple signals, and electrogram (EGM) signals.

A second function of the CEDS is to adjudicate patient return electrode (PRE) connections. The PRE is an electrical large area grounding connection to the body generally used when unipolar energy is delivered from an intracardiac catheter with a small electrode surface area relative to the surface area of the PRE. It normally consists of an electrically conductive patch applied to a posterior location such as the patient's lower back. For example, some equipment may require a PRE connection, whereas other items may not or should not. In the case of contact sensing and lesion assessment, a monitoring instrument may require a unipolar or PRE path to render information regarding catheter electrode contact and lesion quality. On the one hand, PFA or pulsed RF bipolar ablation energy should not have a patient reference connection other than the two bipolar connections in the intracardiac treatment volume, whereas unipolar PFA or pulsed RF ablation energy requires a PRE to return treatment energy back to the generator. Therefore, the CEDS is required to "make" PRE contact during sensing and then "break" PRE contact during bipolar PFA or bipolar pulsed RF ablation.

Further, PFA and pulsed RF each involve the use of high energy in the form of current, voltage, or combinations thereof. As such, the delivery pathway may be vulnerable to degradation and eventual failure. The most likely pathway failure is one that occurs in the catheter, primarily because of the failure of very small-gauge wires within the catheter shaft or failure of the insulation on those wires. The diameter of the catheter shaft is severely constrained by the catheter electrical therapy delivery lumen, which places a limit on the size and quantity of the wires that may be used. During PFA or pulsed RF treatment delivery, the very small-gauge wires are vulnerable to heating and arcing. While a properly designed catheter used in a routine cardiac ablation procedure can be expected to provide nominal performance, a procedure requiring significantly longer time with commensurately greater manipulation may cause the catheter to degrade. Without specific information as to the energy delivery integrity of the pathway, the physician performing a lengthened operation does not know the true condition of the catheter. Thus, the user must either choose to continue delivery treatment energy with a possibly degraded catheter, or decide that the catheter should be exchanged to ensure integrity, which essentially renders the original catheter defective. The second option results in an operation with increased time and expense, as well as increased patient risk. If the user could know specifically the limitations of the potentially degraded or damaged catheter, he or she could proceed and complete the operation and avoid exchange costs and patient risk altogether.

Other than the catheter, other pathway locations may be degraded or damaged. For example, an interconnecting cable may become loose or damaged. It is also possible that the generator delivery section may be degraded or damaged. Another example of failure may occur within the CEDS: a relay used to direct energy may be degraded or damaged (inadvertently latched shut or stuck open). In all of these cases, patient therapy is degraded or ineffective. Worse yet, some of these conditions may pose additional hazards to the patient.

SUMMARY

Some embodiments advantageously provide methods and systems for confirming safe delivery of treatment energy to a patient by identifying a presence of a fault in an energy delivery pathway and identifying a location of the fault within the device. The system may include a processing unit configured to calculate blood impedances external to the device based on known impedance characteristics of the device, and then to calculate impedances within the device during energy delivery based on the calculated blood impedances. The processing unit may prevent the delivery of energy in an energy delivery pathway that is determined to be compromised. The processing unit may also be configured to compare times for two different frequencies to travel a predetermined distance, the difference in the times corresponding to a location of a fault within the energy delivery pathway.

In one embodiment, a system for assessing integrity of an energy delivery pathway may include an energy generator including a processing unit; an electrode distribution system in communication with the energy generator; an impedance measuring device in communication with the electrode distribution system; a medical device in communication with the electrode distribution system including an elongate body having a proximal portion, a distal portion, and a lumen extending between the proximal portion and the distal portion, a treatment element at the distal portion having at least one electrode, and at least one electrode wire, each of the at least one electrode being connected to one of the at least one electrode wire, the energy delivery pathway including at least a part of each of the at least one electrode wire, the energy generator being configured to deliver a first current at a first frequency and a second current and a second frequency to the at least one electrode, the impedance measuring device being configured to: before a delivery of treatment energy from the energy generator, identify a first wire impedance within the device elongate body, a second wire impedance within the device elongate body, and a first shunt admittance within the device elongate body; during the delivery of the first current at the first frequency and the second current at the second frequency, calculate a first blood impedance external to the device elongate body, a second blood impedance external to the device elongate body, and a blood admittance external to the device elongate body based on the determined first wire impedance within the elongate body, the determined second wire impedance within the device elongate body, and the first shunt admittance within the elongate body; during the delivery of the first current at the first frequency and the second current at the second frequency, calculate a third wire impedance within the device elongate body, a fourth wire impedance within the device elongate body, and a second shunt admittance within the device elongate body based on the first blood impedance external to the device elongate body, the second blood impedance external to the device elongate body, and the blood admittance external to the device elongate body; and at least one of: compare the calculated third wire impedance within the device elongate body and the calculated fourth wire impedance within the device elongate body to determine if a fault in the energy delivery pathway exists; and compare the second shunt admittance within the device elongate body to a threshold admittance value to determine if a fault in the energy pathway exists.

In one embodiment, the energy generator may be configured to deliver ablation energy to the at least one electrode, the processing unit being further configured to prevent delivery of the ablation energy to at least one of the at least one electrode when the processing unit determines a fault in the energy delivery pathway exists.

In one aspect of the embodiment, the impedance measuring device may be configured to render a real portion and an imaginary portion of a complex impedance measurement.

In one aspect of the embodiment, the processing unit may calculate the first blood impedance external to the device elongate body, the second blood impedance external to the device elongate body, and the blood admittance external to the device elongate body by: applying a first condition, $i_1 \neq 0$, $i_2 \neq 0$, to the equations:

$$kvl_{i_1}: V_1 = i_1(R_1 + Z_{l,1} + Z_{u,1}) + i_b Z_{u,1};$$

$$kvl_{i_2}: V_2 = i_2(R_2 + Z_{l,2} + Z_{u,2}) + i_b Z_{u,2};$$

$$kvl_{i_b}: 0 = i_b\left(Z_{u,1} + Z_{u,2} + \frac{1}{Y_{sh}}\right) + i_1 Z_{u,1} + i_2 Z_{u,2};$$

and applying a second condition, $i'_1 \neq 0$, $i'_2 = 0$, to the equations:

$$kvl_{i'_1}: V'_1 = i'_1(R_1 + Z_{l,1} + Z_{u,1}) + i'_b Z_{u,1}; \text{ and}$$

$$kvl_{i'_b}: 0 = i'_b\left(Z_{u,1} + Z_{u,2} + \frac{1}{Y_{sh}}\right) + i'_1 Z_{u,1}.$$

In one aspect of the embodiment, the impedance measuring device may calculate the third wire impedance within the device elongate body, the fourth wire impedance within the device elongate body, and the second shunt admittance within the device elongate body by: applying a first condition, $i_1 \neq 0$, $i_2 \neq 0$, to the equations:

$$kvl_{i_1}: V_1 = i_1(R_1 + Z_{l,1} + Z_{u,1}) + i_b Z_{u,1};$$

$$kvl_{i_2}: V_2 = i_2(R_2 + Z_{l,2} + Z_{u,2}) - i_b Z_{u,2}; \text{ and}$$

$$kvl_{i_b}: 0 = i_b\left(Z_{u,1} + Z_{u,2} + \frac{1}{Y_{sh}}\right) + i_1 Z_{u,1} - i_2 Z_{u,2};$$

and applying a second condition, $i'_1 = 0$, $i'_2 = 0$, to the equations:

$$kvl_{i'_1}: V'_1 = i'_1(R_1 + Z_{l,1} + Z_{u,1}) + i'_b Z_{u,1}; \text{ and}$$

$$kvl_{i'_b}: 0 = i'_b\left(Z_{u,1} + Z_{u,2} + \frac{1}{Y_{sh}}\right) + i'_1 Z_{u,1}.$$

In one embodiment, a system for determining a location within a medical device of a fault in an energy delivery pathway may include an energy generator having a processing unit (for example, a PFA or phased RF ablation energy generator); an electrode distribution system including a processing unit and a complex impedance measuring device, the electrode distribution system being in communication with the energy generator, the complex impedance measuring device having a radiofrequency (RF) generator and being configured to render a real portion, r, and an imaginary portion, jx, of an impedance measurement; a medical device in communication with the electrode distribution system including an elongate body having a proximal portion, a distal portion, and a lumen extending between the proximal portion and the distal portion, a treatment element at the distal portion having at least one electrode, and at least one electrode wire, each of the at least one electrode being connected to one of the at least one electrode wire, the energy delivery pathway including at least a part of each of the at least one electrode wire and having a forward portion and a rearward portion, the radiofrequency generator of the complex impedance measuring device being configured to deliver a first test signal along each of the forward portion and the rearward portion of the energy delivery pathway at a first frequency and a second test signal along each of the forward portion and the rearward portion of the energy delivery pathway at a second frequency, the complex impedance measuring device and the processing unit being configured to: calculate a first complex impedance rendered at the first frequency at a known reference point inside the catheter electrode distribution system but representative of incident and reflected waves in each of the forward and rearward portions of the energy delivery pathway propagating to and returning from the tissue load presented to the catheter as well as incident and reflected waves in the rearward portion of the energy delivery pathway propagating to and returning the energy generator, the incident and reflected waves being perturbed in magnitude and phase by potential defects along the forward and rearward portions of the energy delivery pathway, such as opens or shorts; calculate a second complex impedance rendered at the second frequency at the known reference point inside the catheter electrode distribution system but representative of incident and reflected waves in each of the forward and rearward portions of the energy delivery pathway propagating to and returning from the tissue load presented to the catheter as well as incident and reflected waves in the rearward portion of the energy delivery pathway propagating to and returning the energy generator, the incident and reflected waves being perturbed in magnitude and phase by potential defects along the forward and rearward portions of the energy delivery pathway, such as opens or shorts; and identify a location of a fault in the energy delivery pathway within the system based on the real and imaginary components of each of the first and second complex impedances rendered by the complex impedance measuring device.

In one aspect of the embodiment, the first frequency may be approximately 100 MHz and the second frequency may be approximately 65 MHz.

In one aspect of the embodiment, the impedance measuring device may be configured to identify the location of the fault in the energy delivery pathway by: comparing the real and imaginary components of the first complex impedance to threshold real and imaginary components; and comparing the real and imaginary components of the second complex impedance to the threshold real and imaginary components. In one aspect of the embodiment, the impedance measuring device may be further configured to minimize the root sum square error between the threshold real and imaginary components, the real and imaginary components of the first complex impedance, and the real and imaginary components of the second complex impedance.

In one aspect of the embodiment, the threshold real and imaginary components may include: a threshold real component for a first fault type; a threshold real component for the second fault type; a threshold imaginary component for a second fault type; and a threshold real component for the second fault type. In one aspect of the embodiment, the threshold real and imaginary components may be stored in the processing unit as a look-up table.

In one embodiment, a method of determining a fault type and a fault location within a medical device may include: measuring a first complex impedance at a first frequency; measuring a second complex impedance at a second frequency; determining a first component and a second component of the first complex impedance; determining a first component and a second component of the first complex impedance; comparing the first component and the second component of each of the first and second impedances to a reference first component over distance and a reference second component over distance; and determining a distance from a proximal end of the medical device based on the comparison, the distance from the proximal end of the medical device being the fault location.

In one aspect of the embodiment, the method may further include: comparing the first component and the second component of each of the first and second impedances to a reference first component over distance for a first fault type, a reference second component over distance for the first fault type, a reference first component over distance for a second fault type, and a reference second component over distance for the second fault type; and determining whether the fault is the first fault type or the second fault type based on the comparison.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein:

FIG. 6 shows an exemplary fault series impedance at location $d_f$;

FIG. 7 shows an exemplary fault shunt admittance at location $d_f$;

DETAILED DESCRIPTION

Figure 1:
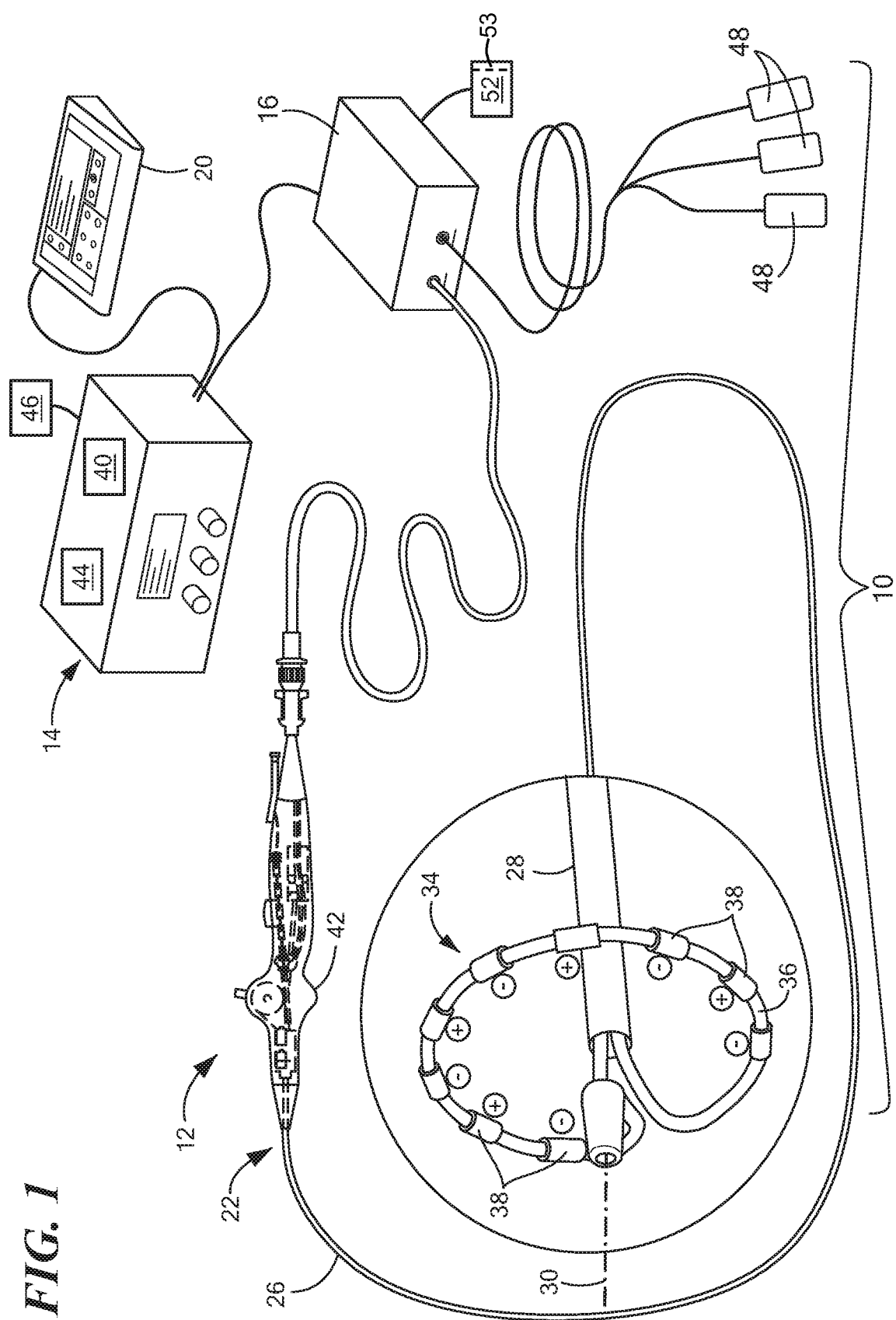
FIG. 1 shows an exemplary system for the delivery of treatment energy.

Before describing in detail exemplary embodiments, it is noted that the embodiments reside primarily in combinations of apparatus components and processing steps related to the safe delivery of treatment energy to a patient. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements.

Referring now to FIG. 1, some embodiments of a medical system 10 for delivering treatment energy include a medical device 12 that may be coupled directly to an energy supply, such as a pulsed electric field or radiofrequency (RF) generator 14 including an energy control, delivering, and monitoring system or indirectly through a catheter electrode distribution system (CEDS) 16. The system 10 may also include a remote controller 20 that is in communication with the generator 14 for operating and controlling the various functions of the generator 14. Further, the medical device 12 may include one or more diagnostic or treatment regions for the energetic, therapeutic, and/or investigatory interaction between the medical device 12 and a treatment site. As a non-limiting example, the device 12 may be a catheter and the treatment region(s) may deliver pulsed field electroporation energy and/or radiofrequency energy to a tissue area in proximity to the treatment region(s).

The medical device 12 may be a treatment device, and may optionally include mapping functionality. The medical device 12 may include an elongate body 22 passable through a patient's vasculature and/or proximate to a tissue region for diagnosis or treatment. For example, the device 12 may be a catheter that is deliverable to the tissue region via a sheath or intravascular introducer (not shown). The elongate body 22 may define a proximal portion 26, a distal portion 28, and a longitudinal axis 30, and may further include one or more lumens 32 disposed within the elongate body 22 thereby providing mechanical, electrical, and/or fluid communication between the elongate body proximal portion 26 and the elongate distal portion 28.

The medical device 12 may further include one or more treatment elements 34 at, coupled to, or on the elongate body distal portion 28 for energetic, therapeutic, and/or investigatory interaction between the medical device 12 and a treatment site or region. As a non-limiting example, the device 12 may include a treatment element 34, such as that shown in FIG. 1, that includes a carrier element 36 bearing a plurality of electrodes 38. The carrier element 36 may be transitionable between a linear configuration and an expanded configuration in which the carrier element 36 has an arcuate or substantially circular configuration. For example, the carrier element 36 may form a loop in the expanded configuration, which may lie in a plane that is substantially orthogonal to the elongate body longitudinal axis 30. Alternatively, the medical device 12 may have a substantially linear configuration with the plurality of electrodes 38 located in a common longitudinal axis along the length of at least a portion of the elongate body distal portion 28 (for example, a focal catheter). However, it will be understood that the device may have any treatment element configuration that is suitable for a particular procedure and that the treatment element configuration may not affect the method described herein.

The plurality of electrodes 38 may also perform diagnostic functions, such as collection of intracardiac electrograms (EGM) and/or monophasic action potentials (MAPs) as well as performing selective pacing of intracardiac sites for diagnostic purposes. Measured signals may be transferred from the catheter electrode energy distribution system (CEDS) 16 to a recording system input box 40, which may be included in or integrated with the generator 14. The plurality of electrodes 38 may also monitor the proximity to target tissues and quality of contact with such tissues using impedance based measurements with connections to the CEDS 16. The CEDS 16 may include high speed relays to disconnect/reconnected specific electrodes 38 from the generator 14 during an energy delivery procedure.

Although not shown, the system 10 may include one or more sensors to monitor the operating parameters throughout the system, in addition to monitoring, recording or otherwise conveying measurements or conditions within the medical device 12 or the ambient environment at the distal portion of the medical device 12. The sensor(s) may be in communication with the generator 14 and/or the CEDS 16 for initiating or triggering one or more alerts or therapeutic delivery modifications during operation of the medical device 12.

The medical device 12 may include a handle 42 coupled to the elongate body proximal portion 26. The handle 42 may include circuitry for identification and/or use in controlling of the medical device 12 or another component of the system. Additionally, the handle 42 may also include connectors that are mateable to the generator 14 and/or the CEDS 16 to establish communication between the medical device 12 and the generator 14 and/or the CEDS 16. The handle 42 may also include one or more actuation or control features that allow a user to control, deflect, steer, or otherwise manipulate a distal portion of the medical device 12 from the proximal portion of the medical device 12.

The generator 14 may include processing circuitry including one or more processing units 44 in communication with one or more controllers and/or memories containing software modules containing instructions or algorithms to provide for the automated operation and performance of the features, sequences, calculations, or procedures described herein and/or required for a given medical procedure. Specifically, each processing unit 44 may have processing circuitry that includes a memory and processor, with the processing circuitry being configured to receive data from the treatment device 12, process data, and to communicate data to a navigation system (not shown) and/or directly the user. As a non-limiting example, the generator 14 may be a GENius® Generator (Medtronic, Inc.) that includes one or more displays 46, user input devices, controllers, data storage units, or the like. Additionally, although the CEDS 16 is shown as being external to the generator 14, it alternatively may be integrated with the generator 14.

The system 10 may further include a plurality of surface ECG electrodes 48 in communication with the generator 14 through the CEDS 16. When the surface electrodes 48 are applied to the skin of a patient, they may be used, for example, to monitor the patient's cardiac activity to determine pulse train delivery timing at the desired portion of the cardiac cycle and/or for navigation and location of the device 12 within the patient. In addition to monitoring, recording, or otherwise conveying measurements or conditions within the medical device 12 or the ambient environment at the distal portion 28 of the medical device 12, additional measurements may be made through connections to the multi-electrode device, such as temperature, electrode-tissue interface impedance, delivered charge, current, power, voltage, work, or the like in the generator 14 and/or the device 12. The surface ECG electrodes 26 may be in communication with the generator 14 for initiating or triggering one or more alerts or therapeutic deliveries during operation of the medical device 12. Additional patient return electrode (PRE) patches (not shown) may be used to evaluate the desired bipolar electrical path impedance, as well as monitor and alert the operator upon detection of undesired and/or unsafe conditions.

The generator 14 may provide electrical pulses to the medical device 12 to perform an electroporation procedure to cardiac tissue or other tissues within the patient's body, such as renal tissue, airway tissue, and organs or tissue within the thoracic or abdominal cavities including the cardiac space. Specifically, generator 14 may be configured and programmed to deliver pulsed, high-voltage electric fields appropriate for achieving desired pulsed, high—voltage ablation (referred to as "pulsed field ablation" or "pulsed electric field ablation") and/or pulsed radiofrequency ablation. As a point of reference, the pulsed, high-voltage, non-radiofrequency, ablation effects of the present disclosure are distinguishable from DC current ablation, as well as thermally-induced ablation attendant with conventional RF techniques. The pulsed-field energy may be sufficient to induce cell death for purposes of completely blocking an aberrant conductive pathway along or through cardiac tissue, destroying the ability of the so-ablated cardiac tissue to propagate or conduct cardiac depolarization waveforms and associated electrical signals. Additionally or alternatively, the generator 14 may be configured and programmed to deliver RF and/or pulsed RF energy appropriate for achieving tissue ablation.

The CEDS 16 may be located adjacent to the patient and may be connected to an implanted device (that is, a device that is located within the patient). Cables of various lengths, for example, between 3 and 10 feet in length, may interconnect the generator 14, CEDS 16, and the device 12. Electrical pathways or transmission lines may exist between the CEDS 16 and device electrodes 38 that present impedances that are unique and discernible depending on defects to the device 12. A complex impedance measuring device 52 (which may be referred to as a "Z-meter") may be located remotely from the device 12 and may be configured to resolve various electrode combinations via the delivery pathway at frequencies in the range of between approximately 1 kHz and approximately 1 MHz. The impedance measuring device 52 may be configured to render a real portion, r, and an imaginary portion, jx, of a complex impedance measurement. The complex impedance measuring device 52 may include an extremely low-level (nanowatt) RF energy generator 53 for delivering test signals at different frequencies along a forward (that is, toward the device 12) and rearward (that is, toward the PFA or pulsed RF generator 14) portion of the energy delivery pathway. The complex impedance measuring device 52 may be in communication with the CEDS 16, or may be a part of the CEDS 16, and may receive signals from the treatment element 34 through the CEDS 16. The impedance measuring device 52 may iteratively measure various electrode combinations such that it can fill a solution matrix with a number of "knowns" sufficient to solve the number of unknowns, such as the device's intrinsic series impedance and shunt admittances. For example, a set of unipolar impedances $Z_{u,1}$, $Z_{u,2}$, ... $Z_{u,n}$ and bipolar admittances $Y_{b,1-2}$, $Y_{b,2-3}$, ... $Y_{b,n-1,n}$ may be accurately determined for blood or tissue in situ, where magnitude and phase impedance and admittance values are used to discern the catheter's condition.

Figure 2:
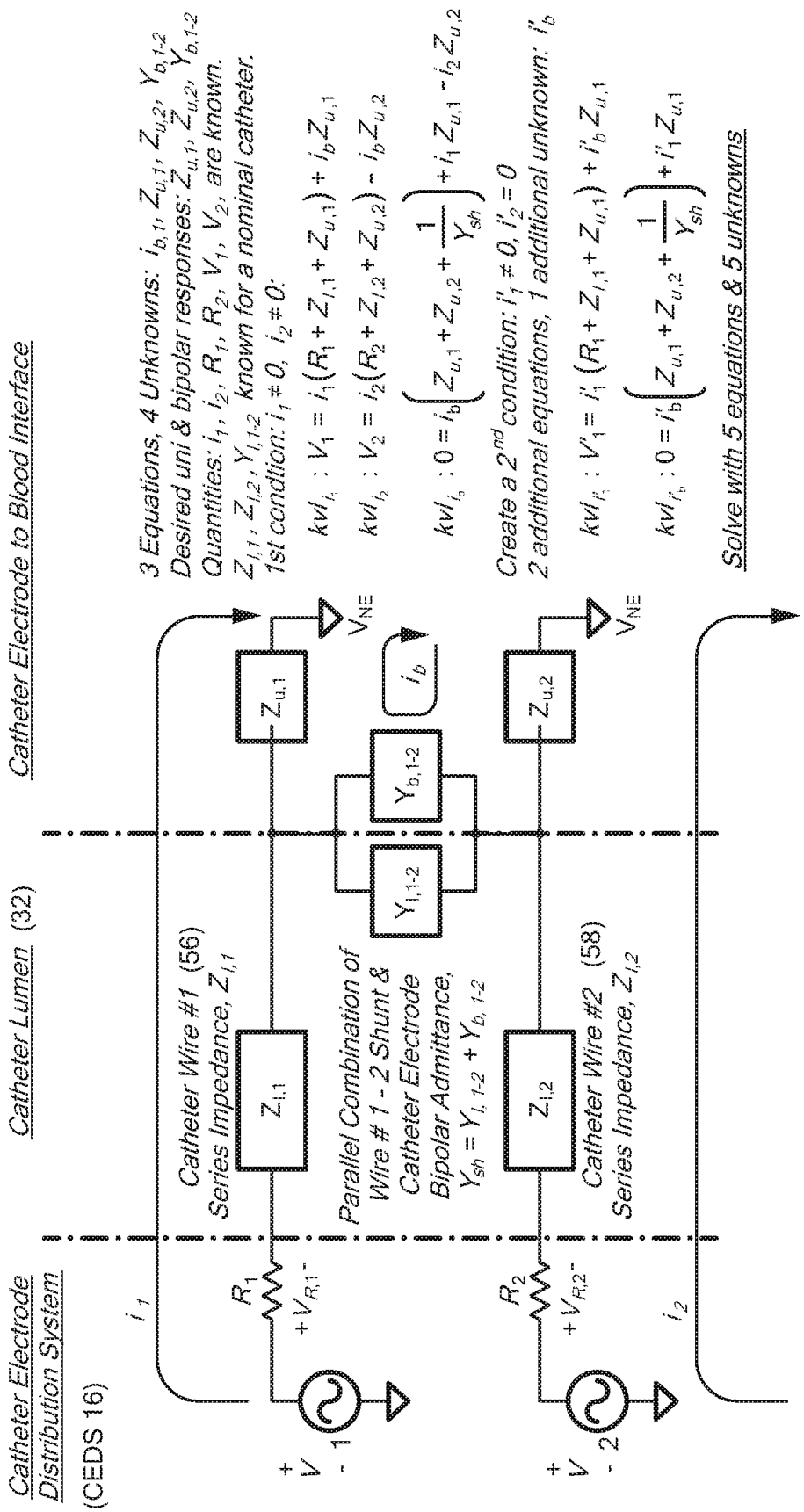
FIG. 2 shows a schematic representation of a delivery electrical pathway for determination of a first set of unknown impedance values.

Referring now to FIG. 2, a schematic representation of a delivery electrical pathway for determination of a first set of unknown impedance values is shown. When the device 12 is in situ prior to ablation, two lumen impedances, $Z_{l,1}$ and $Z_{l,2}$, and a lumen shunt admittance, $Y_{l,1-2}$, are known a priori as a matter of device design and construction, and do not depend on device placement. For example, as shown in FIG. 2, three known values within the device 12 body may be a series impedance, $Z_{l,1}$, for a first wire 56 located within the device elongate body 22 (for example, within a lumen 32), a series impedance, $Z_{l,2}$, for a second wire 58 located within the device elongate body 22 (for example, within the lumen 32), and a parallel combination of a shunt between the first wire and the second wire and device electrode bipolar admittance, $Y_{sh} = Y_{l,1-2} + Y_{b,1-2}$. Each of the first 56 and second 58 wires may be in communication with one or more electrodes 38 and the generator 14. Further, the method described herein may be used for any two wires, regardless of whether they are coupled to the same electrode. As a non-limiting example, each electrode 38 may include two wires, such as a first wire composed of copper or a copper alloy and a second wire composed of constantan, although it will be understood that the wires may be composed of any suitable material. Various combinations of wires may be used for fault detection. For example, a copper first wire of a first electrode may be electrically paired to a copper first wire of a second electrode to determine whether a short exists between them. Additionally or alternatively, a copper first wire of an electrode may be electrically paired to a constantan second wire of the same electrode to ensure that both wires of that electrode are intact.

The process may begin by applying two complex currents $i_1(j\omega)$ and $i_2(j\omega)$ (which may be later abbreviated as $i_1$ and $i_2$) at frequencies of interest via a first voltage source 64, $V_1(j\omega)$, and a second voltage source 66, $V_2(j\omega)$, located within the generator 14. Three initial equations may be used to determine impedance at the device-to-blood (or device-to-tissue), shown below. The values $i_1$, $i_2$, $R_1$, $R_2$, $V_1$, and $V_2$ are known. Additionally, as discussed immediately above, values $Z_{l,1}$, $Z_{l,2}$, and $Y_{l,1-2}$ are known. The value $Y_{l,1-2}$ represents the admittance introduced into the impedance measuring device 52. There initially may be four unknown values: $i_b$, $Z_{u,1}$, $Z_{u,2}$, and $Y_{b,1-2}$. The value $i_b$ represents bipolar current flowing through a loop between two device electrodes 38 via tissue and/or blood. The values $Z_{u,1}$ and $Z_{u,2}$ represent the unipolar impedances of the two electrodes 38 and $Y_{b,1-2}$ is the bipolar admittance between the two electrodes 38 introduced into the device 12 (including the elongate body 22 and device cables). To determine these unknown values, a first condition may be applied by the processing unit 44: $i_1 \neq 0$, $i_2 \neq 0$. The three initial equations are:

$$kvl_{i_1}: V_1 = i_1(R_1 + Z_{l,1} + Z_{u,1}) + i_b Z_{u,1} \quad (1)$$

$$kvl_{i_2}: V_2 = i_2(R_2 + Z_{l,2} + Z_{u,2}) + i_b Z_{u,2} \quad (2)$$

$$kvl_{i_b}: 0 = i_b\left(Z_{u,1} + Z_{u,2} + \frac{1}{Y_{sh}}\right) + i_1 Z_{u,1} - i_2 Z_{u,2} \quad (3)$$

where $V_1$ represents the known voltage of the first voltage source 64, $V_2$ is the known voltage of the second voltage source 66, $R_1$ represents a known resistance value of the first wire 56, $R_2$ represents a known resistance value of the second wire 58, $Z_{l,1}$ represents the known series impedance of the first wire 56, $Z_{l,2}$ represents the known series impedance of the second wire 58, $Z_{u,1}$ represents an unknown first blood impedance, $Z_{u,2}$ represents an unknown second blood impedance, $i_b$ represents bipolar current flowing through a loop between two device electrodes 38 via tissue and/or blood. Primed variables (for example, $i'_1$) represent the same electrical measurements as their non-primed counterparts, but are generated using a second measurement condition, and are included to balance the unknown values with the same number of equations. Further, the admittance term, $Y_{sh}$, is the parallel combination of leakage or conductance between the first 56 and second 58 wires and the blood admittance between the first and second electrodes 38, or:

$$Y_{sh} = Y_{l,1-2} + Y_{b,1-2} \quad (4)$$

Equations (1), (2), and (3) contain four unknown variables. To resolve the unknowns, at least one more orthogonal equation is necessary. Therefore, a second condition may be applied by the processing unit 44 as: $i'_1 \neq 0$, $i'_2 = 0$. Since the system shown schematically in FIG. 2 is linear and time invariant, a set of linear equations can be assigned to the circuits and solved to find the desired impedances, $Z_{u,1}$, $Z_{u,2}$, and $Y_{b,1-2}$. By setting the current $i'_2$ to zero, two more equations with only one additional unknown value, $i'_b$, are generated:

$$kvl_{ir_1}: V'_1 = i'_1(R_1 + Z_{l,1} + Z_{u,1}) + i'_b Z_{u,1} \quad (5)$$

$$kvl_{ir_b}: 0 = i'_b\left(Z_{u,1} + Z_{u,2} + \frac{1}{Y_{sh}}\right) + i'_1 Z_{u,1} \quad (6)$$

where $V'_1$ represents the known voltage of the first voltage source 64, $i'_1$ represents the first complex current, $R_1$ is a known resistance value of the first wire 56, $Z_{l,1}$ is the known series impedance of the first wire 56, $Z_{u,1}$ is the unknown first blood impedance, $Z_{u,2}$ is the unknown second blood impedance, $i'_b$ represents bipolar current flowing through a loop between two device electrodes 38 via tissue and/or blood, and $Y_{sh}$ is the parallel combination of the unknown leakage or conductance between the first 56 and second 58 electrode wires, $Y_{l,1-2}$, and the known blood admittance between the first and second electrodes 38, $Y_{b,1-2}$.

The resulting set includes five equations and five unknown values for which a numerical solution can be obtained at each frequency component or current using one or more algorithms executed by the processing unit 44. Once all the impedance values shown in FIG. 2 are resolved, and considering that the blood impedances, $Z_{u,1}$, $Z_{u,2}$, and $Y_{b,1-2}$ are constant prior to and after an ablation procedure, it is possible to establish a new system, shown schematically in FIG. 3, to determine whether shifts have occurred to the lumen wire impedances, which would then indicate catheter degradation or damage.

Figure 3:
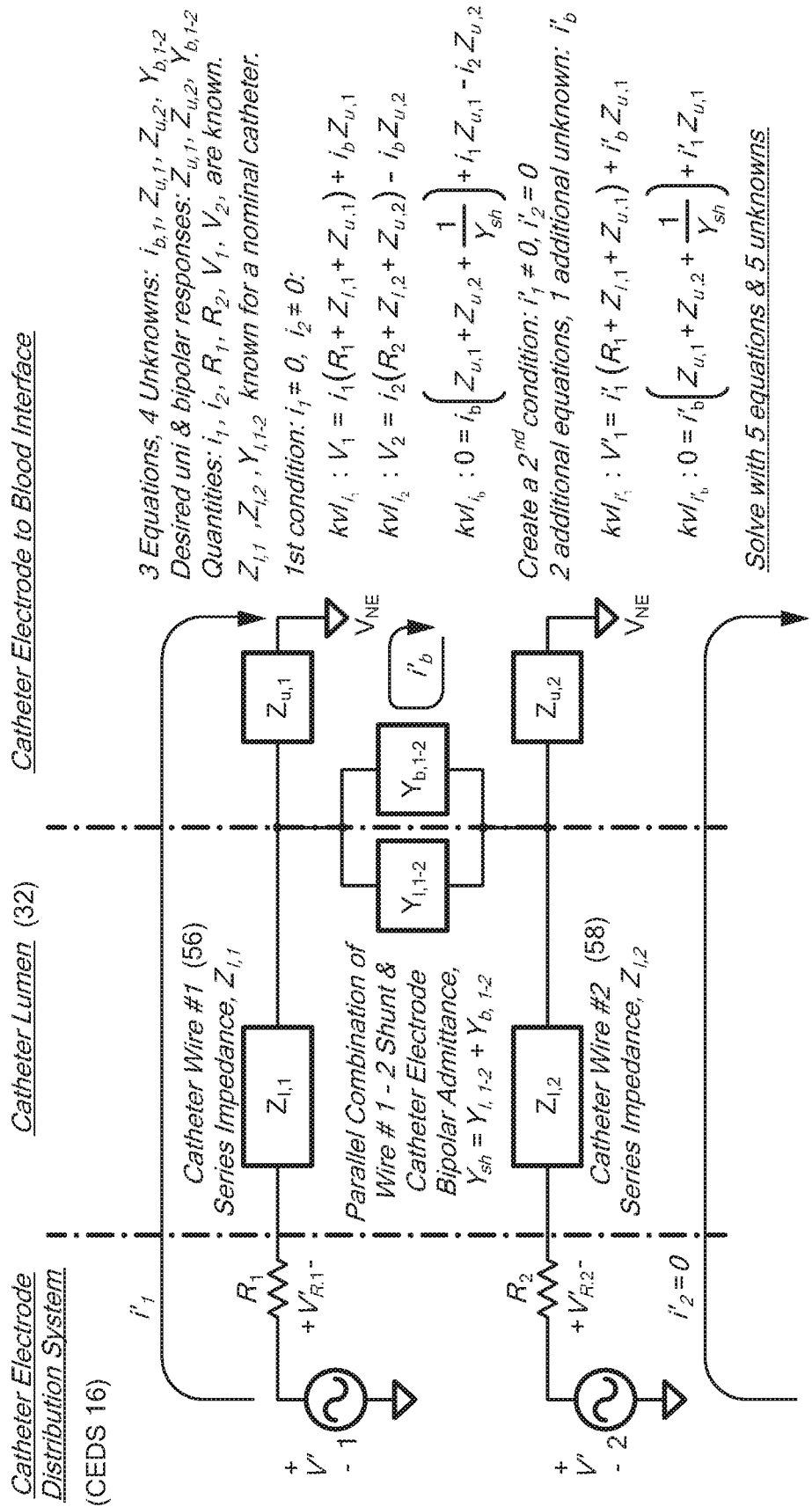
FIG. 3 shows a schematic representation of a delivery electrical pathway for determination of a second set of unknown impedance values.

Referring to FIG. 3, a schematic representation of a delivery electrical pathway for determination of a second set of unknown impedance values is shown. In this case, the blood impedance values, $Z_{u,1}$, $Z_{u,2}$, and $Y_{b,1-2}$ are known from the calculations discussed in relation to FIG. 2, whereas the device lumen impedance values, $Z_{l,1}$, $Z_{l,2}$, and $Y_{l,1-2}$ are unknown. To determine these unknown values, the first condition may be applied ($i_1 \neq 0$, $i_2 \neq 0$) and the three initial equations, (1), (2), and (3), may be executed by the processing unit 44. The second condition may be applied ($i'_1 \neq 0$, $i'_2 = 0$), the current $i_2$ may again be set to zero, and the two additional equations, (4) and (5), may be created.

The resulting set includes give five equations and five unknown values for which a numerical solution can be obtained at each frequency component or current using one or more algorithms executed by the processing unit 44. Once all the impedance values shown in FIG. 3 are resolved, the processing unit 44 may determine whether shifts have occurred to the lumen wire impedances, which would then indicate catheter degradation or damage.

Slight changes to the lumen wire 56, 58 impedance values are normal and may not be indicative of a degraded device 12. On the other hand, significant changes, such as greatly increased admittance value (as compared, for example, to a predetermined threshold admittance value), $Y_{sh}$, between a wire pair may indicate a partial or complete short circuit has occurred. Likewise, a significant increase in the series impedance component, $Z_{l,1}$ or $Z_{l,2}$, relative to each other or over a predetermined threshold impedance value may indicate that a wire 56, 58 has overheated with high resistance or has open circuited. As a result, the processing unit 44 is able to verify the pathway signal integrity and prevent ablation energy from being delivered to the damaged portion of the device 12. The generator 14 may then inform the user, such as through the one or more displays 46, to rotate the device 12 to an electrode position with verified signal integrity and continue to deliver ablation energy to the tissue. By continuing to deliver ablation energy with a partially damaged device, the user avoids the time, expense, and patient risks associated with a catheter exchange. In other words, risks associated with energy delivery from the partially damaged device when the device is in the new electrode position recommended by the system are outweighed by the risks associated with device replacement during the procedure.

Figure 4:
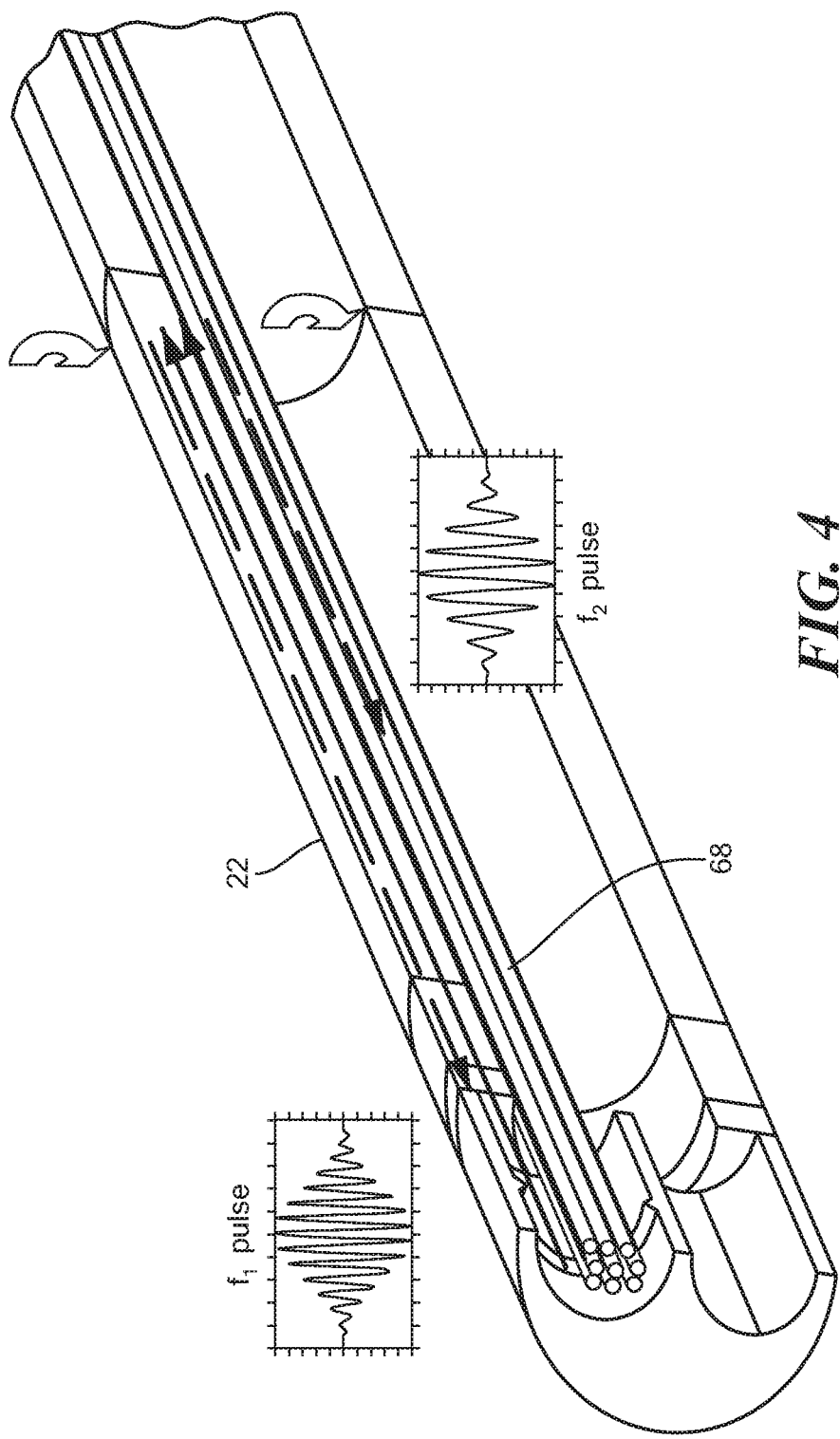
FIG. 4 shows a first cross-sectional view of a portion of an exemplary treatment device with a fault.

Referring now to FIG. 4, a cross-sectional view of an exemplary portion of a treatment device is shown. Specifically, a portion of the elongate body between the handle 42 and the treatment element 34 is shown. The device 12 may be as shown and described in FIG. 1, or may be a treatment device having a treatment element with a different configuration than that shown in FIG. 1. The device 12 may generally include an elongate body 22 having a proximal portion 26, a distal portion 28, one or more lumens, and a plurality of wires 68 (which may include the first 56 and second 58 wires discussed herein) within a lumen 32 that are in communication with one or more electrodes 38 of the treatment element 32 and the generator 14.

Although impedance may be used to identify a normal condition or a fault in the form of an open or short, such technique does not identify the specific location of the fault. Frequency domain reflectometry, on the other hand, does provide information about the location of the fault within the device, and may be used instead of temperature readings from thermocouples to identify that location. Using this information, a user may quickly remedy the problem causing the fault during a procedure. As a non-limiting example, a fault location is represented with an "X" in FIG. 4. Electromagnetic waves are known to propagate along wires implanted or located within in the human body. From research in the area of magnetic resonance imaging, waves propagating along transmission wires implanted or located within the human body in the very low, medium, high, and very high frequency ranges (VLF, MF, HF, and VHF, between 30 KHz and 300 MHz) exhibit a near constant guide wave propagation constant vector, $\vec{k}_g$ according to the equation:

$$\vec{k}_g = \frac{2\pi}{\lambda_g}\vec{a}_z \quad (7)$$

where $\vec{k}_g$ is along a path of the wire, or longitudinal $\vec{a}_z$ direction, and is inverse to the guide wavelength of the propagating mode of energy.

Figure 5:
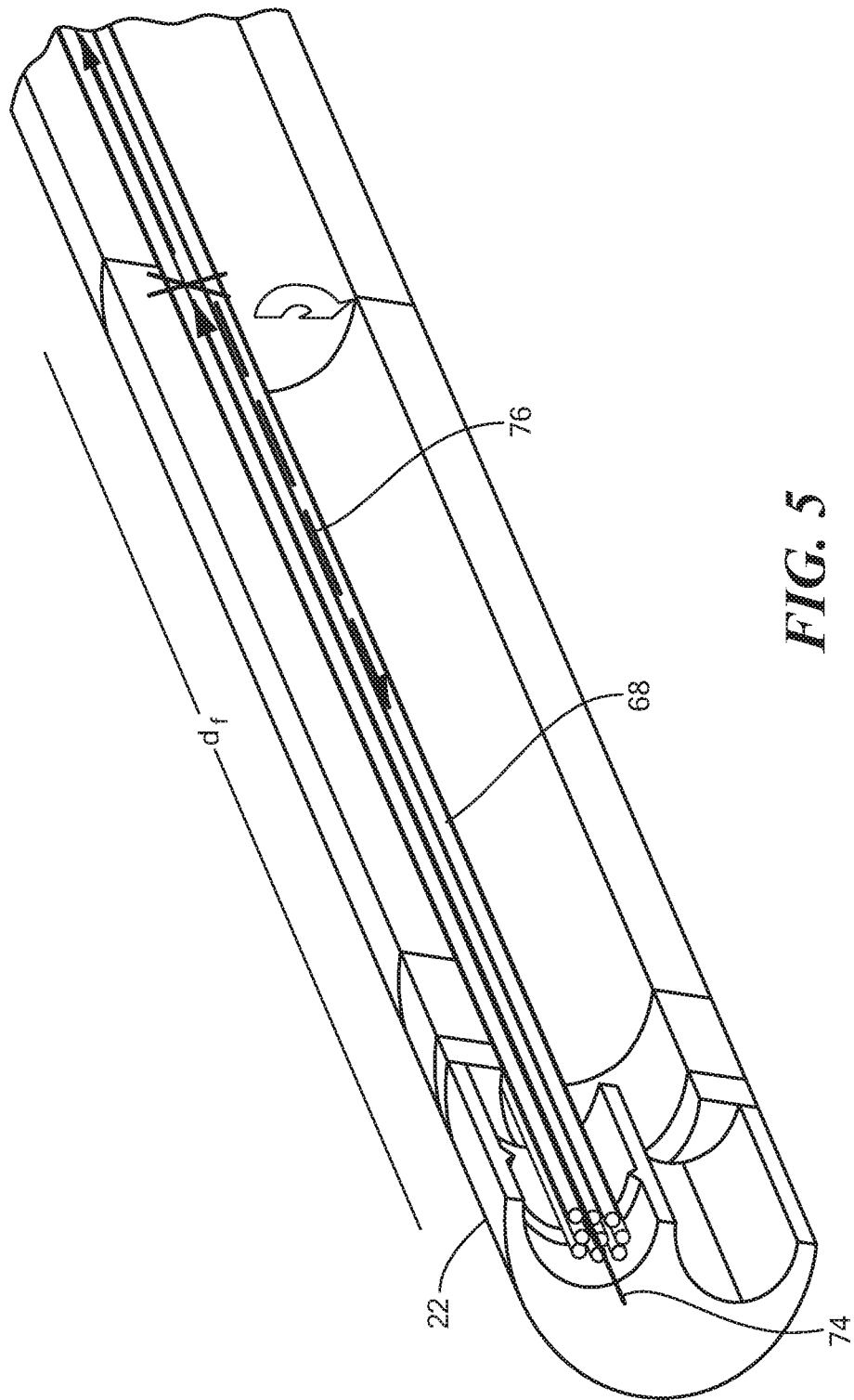
FIG. 5 shows a second cross-sectional view of a portion of an exemplary treatment device with a fault.

For the case of propagating waves inside a device lumen, there are two important properties of the wave vector $\vec{k}_g$. First, $\vec{k}_g$ is strongly related to the catheter construction and design; therefore, it may be considered to be an a priori performance constant. Second, the fact that a wave propagates through a uniform cross section inside a device lumen as it traverses from the proximal to distal end implies that $\vec{k}_g$ is constant along the length of the device. Therefore, the wave will propagate predictably according to the design and construction of the catheter and also to the laws and relations governing radio frequency (RF) transmission line theory. Consider the system shown in FIG. 5. An extremely low power RF source from an impedance measuring device (on the order of nanowatts and incapable of causing patient injury) propagates along the catheter differential wire pair (the first 56 and second 58 wires). The distal wave (shown in FIG. 5 as solid line 74) first encounters a catheter wire impairment or discontinuity at distance $d_{fault}$ or $d_f$, where a portion of the wave reflects back toward the proximal end (shown in FIG. 5 as dashed line 76). Some of the energy continues to the distal electrode termination (solid line) and is dissipated, but also reflected from there (dashed line). Regardless of the overall energy absorption and reflection mechanisms, a unique impedance measurement is rendered at the proximal end. From the measured proximal impedance and transmission line properties, the location of the fault can be determined using the fact that the blood admittance and transmission line properties are known at two evaluation frequencies. Then, using a linear system of equations or ABCD parameters, it is possible to express the impedance presented at the proximal end as a function of the catheter wire transmission line properties, the fault series impedance, $Z_{ser-fault}$ (a non-limiting example is shown in FIG. 6), or fault shunt admittance, $Y_{sh-fault}$ (a non-limiting example is shown in FIG. 7) and the location of the fault, $d_f$, the catheter length, d, and the blood admittance as:

$$Z_{in} = \frac{R(1,1)}{R(2,1)} \quad (8)$$

where the 2×1 matrix [R] is the product of three 2×2 matrix elements and the 2×1 tested pathway transmission equation with the blood admittance termination vector:

$$[R] = [xmsn_1][z_f][xmsn_2]\begin{bmatrix} z_{bip} \\ 1 \end{bmatrix} \quad (9)$$

The individual section matrices are given as:
(a) the 2×2 transmission line matrix [xmsn$_1$] preceding the fault is expressed as:

$$[xmsn_1] = \begin{bmatrix} \frac{e^{k_g d_f} + e^{-k_g d_f}}{2} & \frac{z_o(e^{k_g d_f} + e^{-k_g d_f})}{2} \\ \frac{e^{k_g d_f} + e^{-k_g d_f}}{2z_o} & \frac{e^{k_g d_f} + e^{-k_g d_f}}{2} \end{bmatrix} \quad (10)$$

(b) the 2×2 matrix [$z_f$] is the presumptive series fault matrix:

$$[z_{f-ser}] = \begin{bmatrix} 1 & z_{ser} \\ 0 & 1 \end{bmatrix} \quad (11)$$

or shunt fault matrix:

$$[z_{f-sh}] = \begin{bmatrix} 1 & 0 \\ Y_{sh} & 1 \end{bmatrix} \quad (12)$$

(c) the 2×2 transmission line matrix [xmsn$_2$] following the fault is expressed as:

$$[xmsn_2] = \begin{bmatrix} \frac{e^{k_g(d-d_f)} + e^{-k_g(d-d_f)}}{2} & \frac{z_o(e^{k_g(d-d_f)} - e^{-k_g(d-d_f)})}{2} \\ \frac{e^{k_g(d-d_f)} + e^{-k_g(d-d_f)}}{2z_o} & \frac{e^{k_g(d-d_f)} + e^{-k_g(d-d_f)}}{2} \end{bmatrix} \quad (13)$$

(d) and the electrode impedance in blood is given as:

$$[z_f] = \begin{bmatrix} z_{bip} \\ 1 \end{bmatrix} \text{ where:} \quad (14)$$

$$z_{bip} = \frac{1}{y_{bip}} \quad (15)$$

When describing a transmission line, the wave propagation vector may be expressed as a complex exponential consisting of a loss, α, and wavelength term, β:

$$k_g = \alpha + j\beta \quad (16)$$

The loss term, α, is given in terms of nepers per unit length and usually derived from decibel loss per some arbitrary length:

$$\alpha = -\log\left(10^{\frac{loss_{dB}}{20}}\right), \text{ nepers per unit length} \quad (17)$$

and the wavelength term is given as:

$$\beta = \frac{2\pi}{k_o vp}, \text{ radians per unit length} \quad (18)$$

where $k_o$ is the free-space wave vector, and vp is the velocity of propagation in the medium, in this case, a pair of wares from a larger group located inside a catheter lumen.

Therefore, given a priori knowledge of the guide wave properties of the lumen 32, it is possible to accurately determine the distance to a reflection caused by an open or short circuit by measuring the impedance from the proximal side, $z_{in}$. To perform the measurement, the complex impedance measurement device 52 applies a very low power sin wave at an evaluation frequency (50<f<100 MHz) and measures a complex impedance in the form of real and imaginary components, or:

$$z(j\omega) = r + jx \quad (19)$$

By using nanowatt power and a spectrally efficient sin wave source instead of a broad spectrum unit step pulse that is used in time domain reflectometry, this method requires far less power, typically much less than 10 μA as required by regulatory authority, which limits patient current to safe levels.

Figure 8:
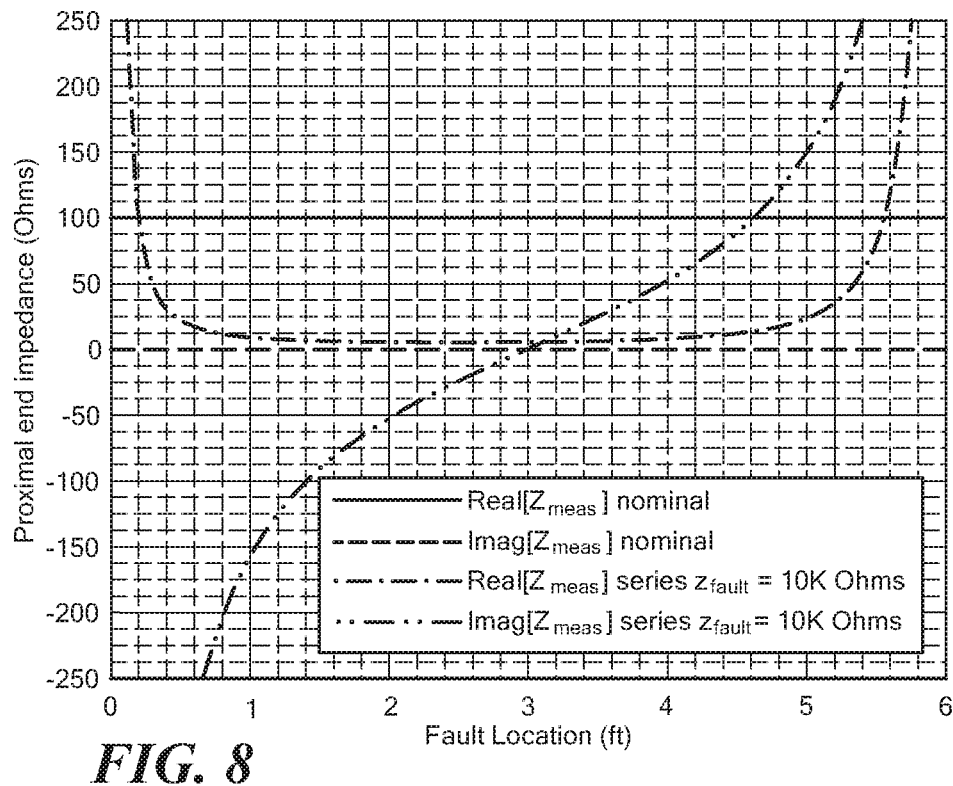
FIG. 8 shows a graphical view of a comparison between proximal-end measured impedance at 65 MHz of a nominal device and a device having a 10K-Ohm open fault condition.
Figure 9:
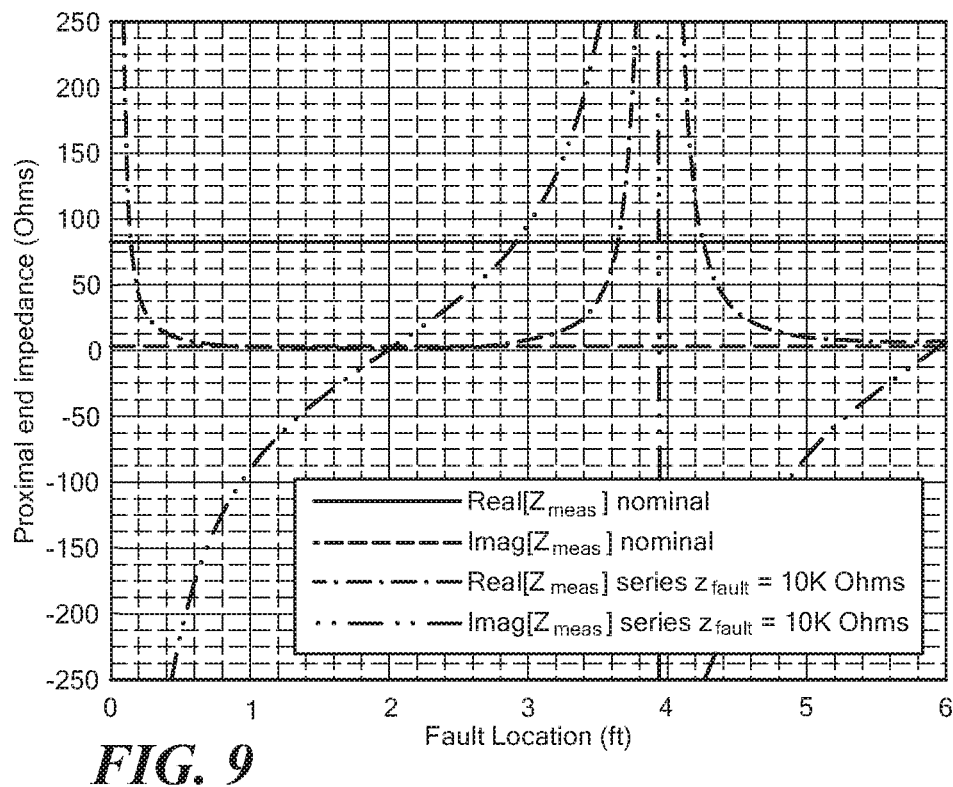
FIG. 9 shows a graphical view of a comparison between proximal-end measured impedance at 100 MHz of a nominal device and a device having a 10K-Ohm open fault condition.
Figure 10:
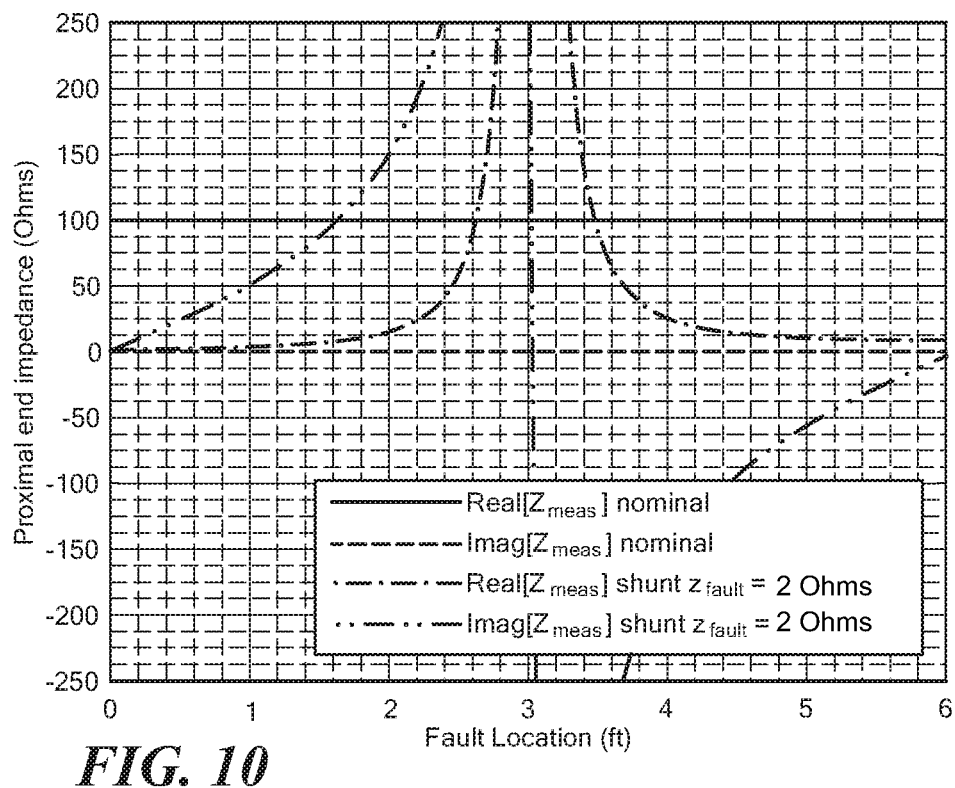
FIG. 10 shows a graphical view of a comparison between proximal-end measured impedance at 65 MHz of a nominal device and a device having a 2-Ohm shorted fault condition.
Figure 11:
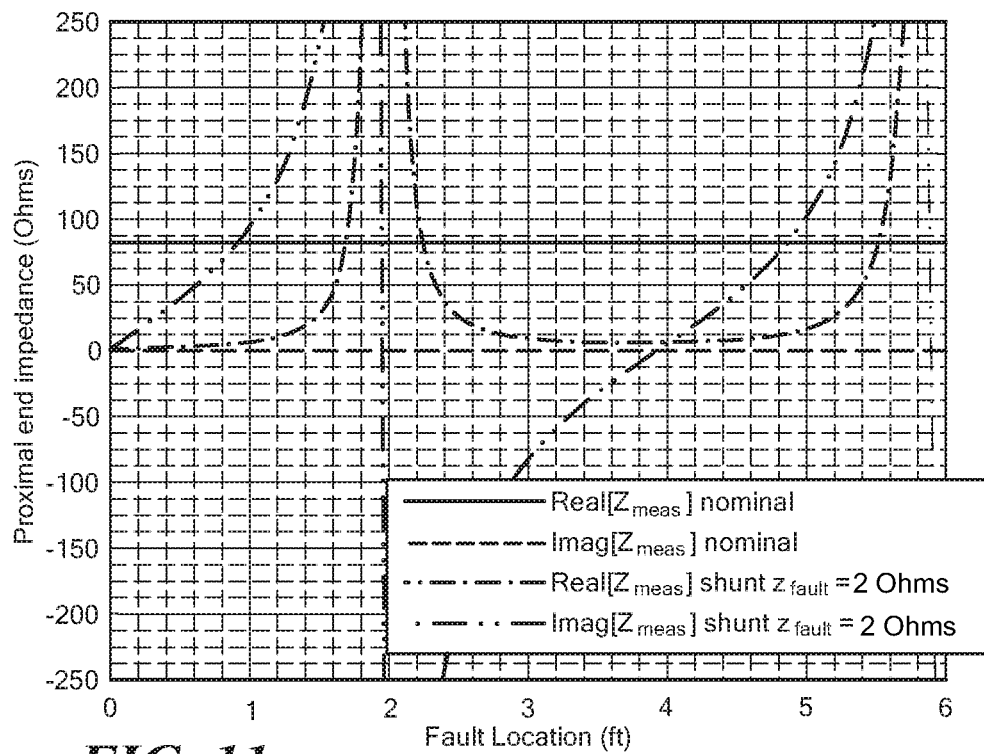
FIG. 11 shows a graphical view of a comparison between proximal-end measured impedance at 100 MHz of a nominal device and a device having a 2-Ohm shorted fault condition.

Assuming that the fault is either in the form of a partial or complete open, or a partial or complete short, both the fault impedance magnitude and location are discernible. FIG. 8 shows a proximal-end measured impedance at 65 MHz of a normal or unbroken device (referred to herein as a nominal catheter) and a faulty device (in the examples given herein, the device may be a catheter) with a 10K-Ohm "open" fault (series $r_{fault}$>1 M Ohm) in relation to distance (distance $d_1$). FIG. 9 shows a proximal-end measured impedance at 100 MHz of a nominal catheter and a faulty catheter with a 10K-Ohm "open" fault in relation to distance. FIG. 10 shows a proximal-end measured impedance at 65 MHz of a nominal catheter and a faulty catheter with a 2-Ohm "shorted" fault in relation to distance. FIG. 11 shows a proximal-end measured impedance at 100 MHz of a nominal catheter and a faulty catheter with a 2-Ohm "shorted" fault in relation to distance. The processing unit 44 and/or the impedance measuring device 52 may compare the proximal-end measured impedances with the proximal-end impedances of the nominal catheter to determine whether a fault condition is present. In other words, the known proximal-end measurements of the nominal catheter may be used as threshold or reference measurements for comparison to the measured impedances from a potentially faulty device.

While the nominal catheter's real and imaginary impedance remains relatively constant versus $d_1$, both real and imaginary impedance components of the faulty catheter differ considerably from the nominal catheter's impedance. For example, if the real part of the measured impedance of the faulty catheter, $\text{Re}\{Z_{meas,F=65M}\}$, approximately equals 3 Ohms at 65 MHz, and the imaginary component of the faulty catheter, $\text{Im}\{Z_{meas,F=65M}\}$, approximately equals—150 Ohms at 65 MHz, then the fault location is nearly one foot from the proximal end, and the impairment is an open or wire break. Another otherwise normal wire pair may render a nearly constant real impedance of 100 Ohms, with a negligible reactance, or $\text{Im}\{Z_{meas}\}\sim 0$ Ohms.

Yet, unless impedance is tested at a second frequency, a single frequency result may leave a fault ambiguous as to its type (that is, short or open) and location. The user would know only that they have an "open" fault at location "A," or a "shorted" fault at location "B," for example. The following method may be used to remove this ambiguity and provide for a single-fault solution. Assume that an "open" or series fault exists one foot from the proximal end of the elongate body. According to the 65 MHz graph in FIG. 8, the real impedance component would be slightly greater than zero ($\text{Re}\{Z_{in,F=65M}\}\sim 3$ Ohms) and the imaginary impedance component ($\text{Im}\{Z_{in,F=65M}\}$) would be approximately—150 Ohms. Referring to the 65 MHz graphs in FIG. 10, this result is ambiguous with a "short" located two feet from the distal end of the elongate body (or approximately four feet from the proximal end), because its impedance at the proximal end of the elongate body would be nearly the same. This ambiguity may be resolved by measuring the wire pair at a second frequency. For example, if the proximal end input impedance were measured at 100 MHz, then the same "open" fault would resolve for its real component as $\text{Re}\{Z_{in,F=100M}\}$ approximately equal to 2 Ohms, whereas the imaginary component would decrease to $\text{Im}\{Z_{in,F=100M}\}$ approximately—100 Ohms. This result is no longer ambiguous with a "short" two feet from the distal end since the imaginary portion (if it were actually a "short") would then need to resolve as $\text{Im}\{Z_{in,F=100M}\}\sim 0$ Ohms, which is quite dissimilar to the actual measured "open" result at 100 MHz, $\text{Im}\{Z_{in,F=100M}\}$ equal to—100 Ohms. Therefore, the only correct inference is that an "open" or series fault occurred one foot from the proximal end of the elongate body.

The generator processing unit 44 may include a microcontroller with a set of coded instructions for executing the algorithm for this method. The microcontroller may first configure the generator relays and signal paths to present the desired pathway, that pathway being forward from the electrode distribution system to the medical device or catheter 12, or a rearward pathway back to the PFA or RF ablation energy generator 14. Next, the microcontroller may instruct the impedance measuring device 52 to perform an impedance measurement of the selected signal path at two frequencies (for example, between 50 and 100 MHz). The microcontroller may then compare the following four values to a pre-tabulated list of open and short impedances for the first and second frequency and given pathway: (1) the proximal end real impedance component rendered at the first frequency; (2) the proximal end imaginary impedance component rendered at the first frequency; (3) the corresponding proximal end real impedance component rendered at the second frequency; and (4) the corresponding proximal end imaginary impedance component rendered at the second frequency. Then, by correlation by minimizing the root sum square error between a nominal table set of the four impedances and the measured data, the microcontroller may identify the type of fault and its location.

While the process described above was discussed regarding an exemplary catheter with an "open" or "shorted" fault, the same process may be applied to the system 10 as a whole, rather than just the device 12 used with the system. For example, a rearward pathway may be established between the CEDS 16, the interconnecting cable between the CEDS 16 and the PFA or RF generator 14, and continuing inside the generator 14 up to a half bridge system 80 (referred to in FIG. 12 as the H bridge) within the generator's energy delivery circuit. Similar to the catheter pathway transmission of Equation (9), this system is constructed by chaining together the terms that can be seen by inspection of FIG. 12. While Equation (20) does not contain a fault term, a presumption "open" or "short fault, $[Z_f]$, would be added between two of the terms to generate a tabular set of data to store in the microcontroller's coded set of instructions for comparison to an actual system, as shown previously in the catheter fault example and in Equation (9).

$$[R_{CEDS-to-Gen}] = [Z_{CEDS}][Z_{con-CEDS}][xmsn_{G-C}][Z_{con-GEN}] \quad (20)$$

$$[Z_{Rel}]\begin{bmatrix} Z_{HB} \\ 1 \end{bmatrix}$$

Figure 12:
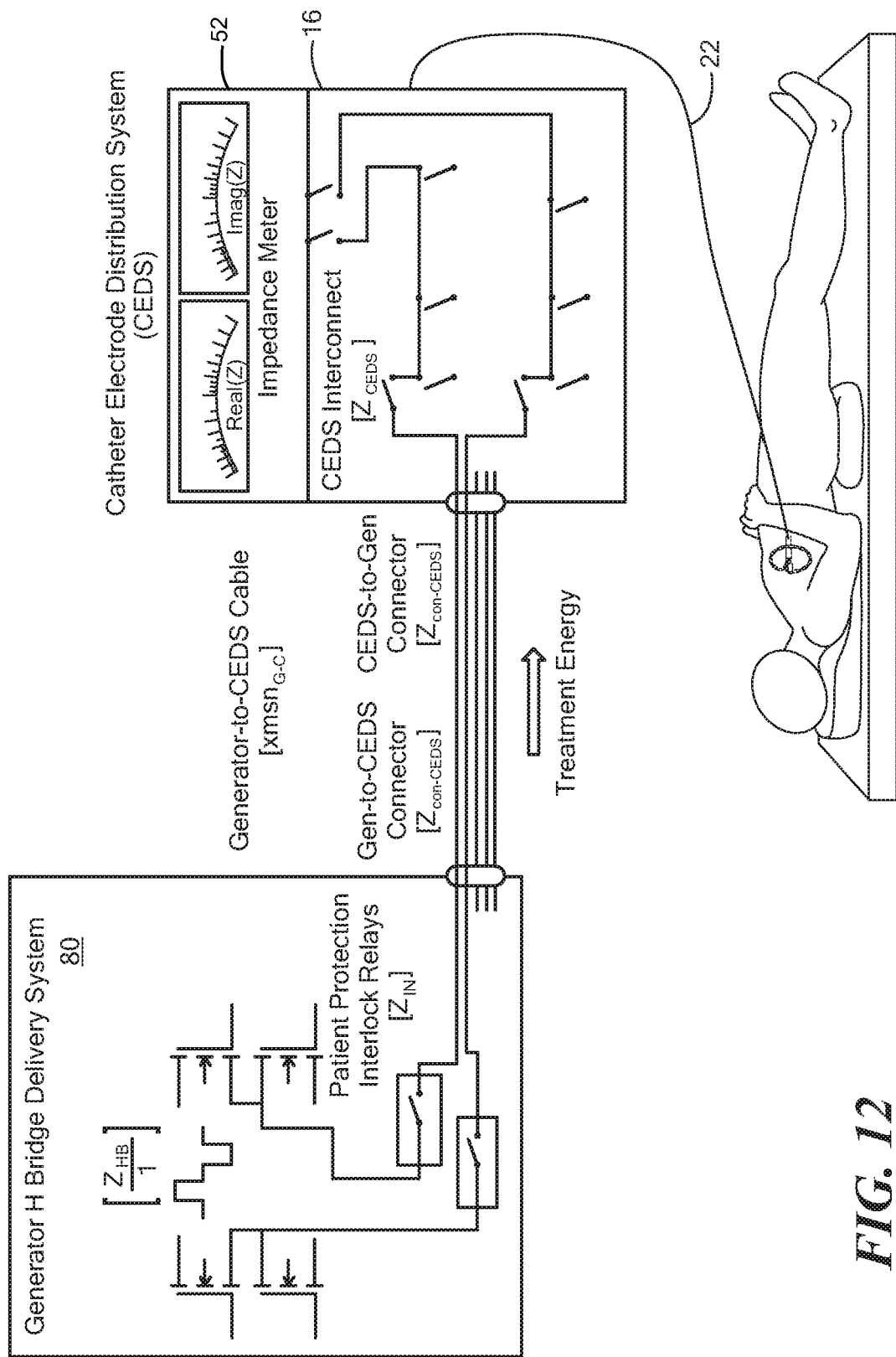
FIG. 12 shows an alternate view of the exemplary system of FIG. 1, illustrating an H bridge in the generator and an impedance meter in the catheter electrode distribution system (CEDS)

The nominal input impedance from the perspective of the impedance meter in FIG. 12 for the CEDS-to-generator pathway may then be found by substitution of the row and column terms as specified in Equation (8):

$$z_{in} = \frac{R_{CEDS-to-Gen}(1,1)}{R_{CEDS-to-Gen}(2,1)} \quad (21)$$

The additional terms in Equation (20) represent discontinuities or radio wave reflection locations at the very high frequency (VHF) test frequencies, typically between 50 MHz and 100 MHz (50 MHz<F<100 MHz). For example, a connector may increase series inductance relative to the cable wire pairs and cause a reflection; therefore, a term and its location should be part of the transmission pathway. Another example is the presence of a large patient protection vacuum relay between the H bridge delivery insulated gate bipolar transistors (IGBTs) and the generator-to-CEDS therapy connection cable. The large relays, although they would not cause a reflection at the audio frequency range PFA treatment energy (that is, they are invisible from a reflectometry standpoint at this frequency), they become more significant with the use of VHF where they would cause a reflection in the tested pathway. However, these discontinuities are readily discoverable in the nominal design as lumped series or shunt impedances and thus are readily managed as terms added to the pathway Equation (20). The terms in Equation (20) are known a priori for a nominal system.

By adding arbitrary series or shunt faults to Equation (20), impedance graphs can be generated similar to those shown in FIGS. 8-11 and then stored in the microcontroller coded instructions in the form of a look-up or reference table for the pathway fault algorithm used to compare actual measurements of the system 10 (for example, a fielded PFA generator system). The resolution of the fault location may be better than one centimeter, assuming evaluation frequencies between 50 MHz and 100 MHz (50 MHz<F<100 MHz), with a nearly 98% probability of determination of a short or open fault condition.

To gain confidence that the system 10 is functioning properly and safe to use, the user may perform a pre-(or post-) operational functional test to confirm that all delivery pathways are in nominal operating condition. Prior to beginning an operation, pathway impairments or faults may occur, such as saline or blood entering the end of the generator-to-CEDS cable and coating the high voltage delivery connections, or by a bent or missing connector pin, or a broken wire in a cable. If any of the aforementioned faults exist, then upon the first delivery of treatment energy, an arc would ensue that could ruin additional pathway components (other than the original fault) such as a cable, connector or generator electronic components. Therefore, a pre-operational test would be useful in identifying such a fault, which in the case of fluid contamination inside a connector, could be easily cleaned and dried. Such a test or check could be applied posthaste of a delivery in which case the generator's fault system identifies and informs the user of inappropriate treatment energy in the form of excessive or insufficient current, charge, or power. An example would be the microprocessor's identification of a fault such as a "short" in a catheter extension cable. By providing the ability to identify the specific location, and thus the specific faulty item, the microprocessor can communicate this information to the user and recommend replacement of the catheter extension cable, rather than providing an ambiguous result that one of three (or more) faults exist: a faulty catheter extension cable, a faulty catheter, or a faulty CEDS. The consequences of the last two failures are serious and pose additional patient risk: a suspected faulty catheter requires explant and replacement in order to complete the PFA treatment procedure; a damaged CEDS could force the user to abort the procedure altogether. Upon the user's replacement of the catheter extension cable, the system may perform a subsequent pathway check to confirm the proper functioning state of the system. The advantage to the customer is a rapid method of providing a specific remedy to an equipment problem, thereby minimizing the user's time and labor required to perform an on-site repair, which in the case of an in-progress intracardiac operation, would be imperative.

Further, not only can the RF pulses be differentiated by frequency, but they may also be differentiated by delivery patterns. In the case of a multi-conductor lead, similar sets of pulses may be applied to all electrodes 38. For example, for a device having nine electrodes (E1-E9), energy may be delivered to the electrodes 38 in the following pattern: E1 to E2, E2 to E3, E3 to E4, E4 to E5, E5 to E6, E6 to E7, E7 to E8, and E8 to E9. Faults may be identified by examining the various electrode combinations.

Figure 13:
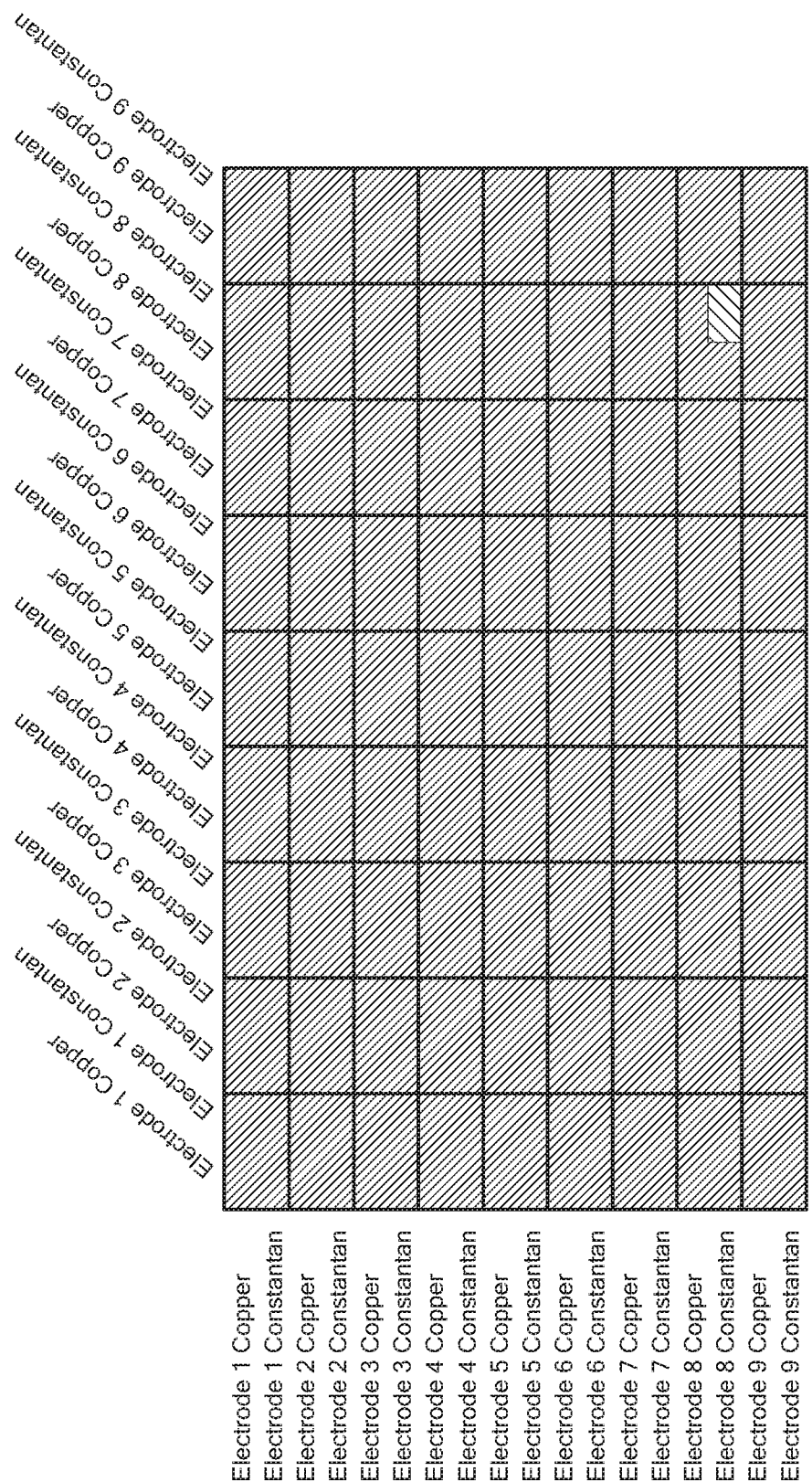
FIGS. 13 and 14 shows exemplary informational displays in which information is presented in a matrix.
Figure 14:
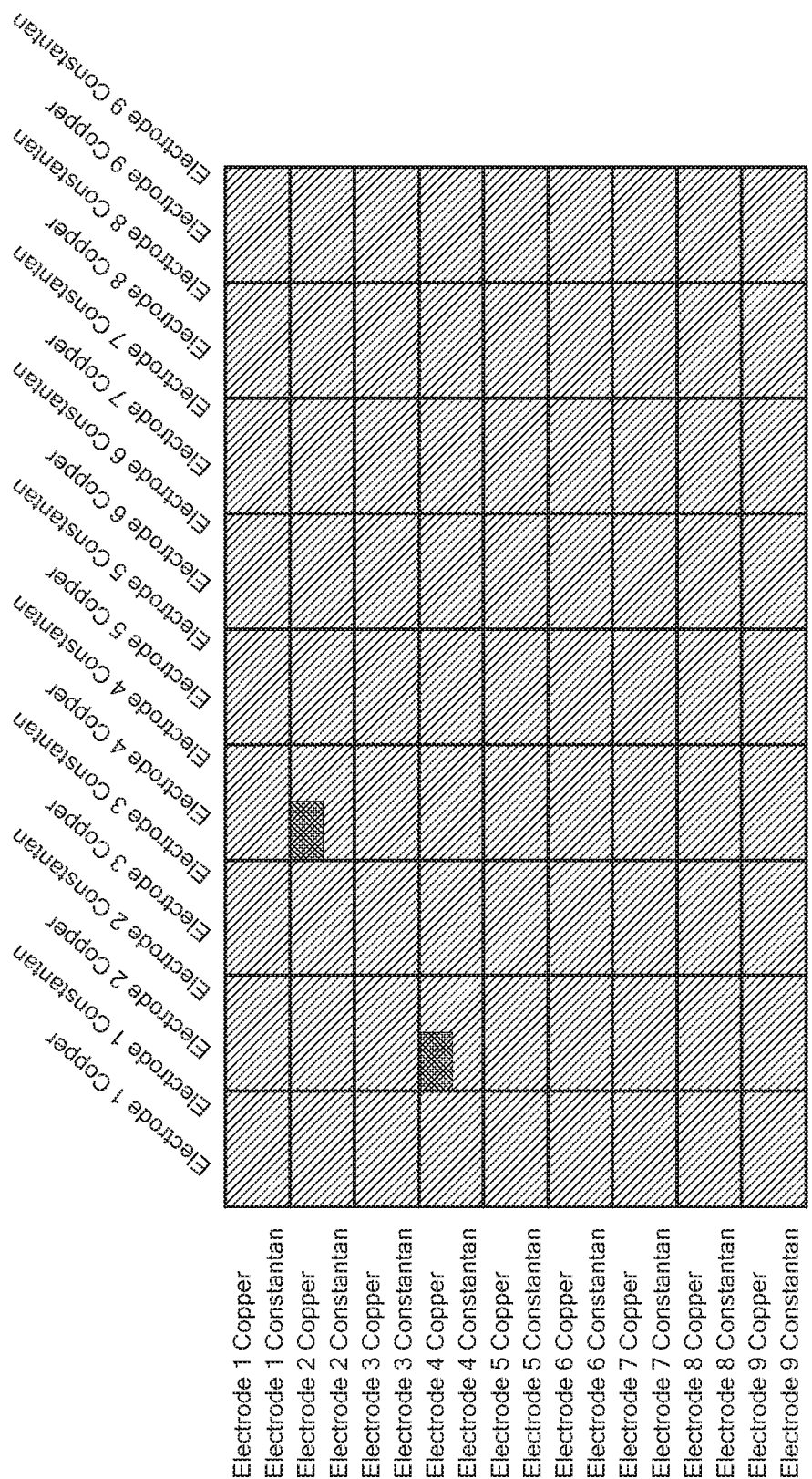
Figure 15:
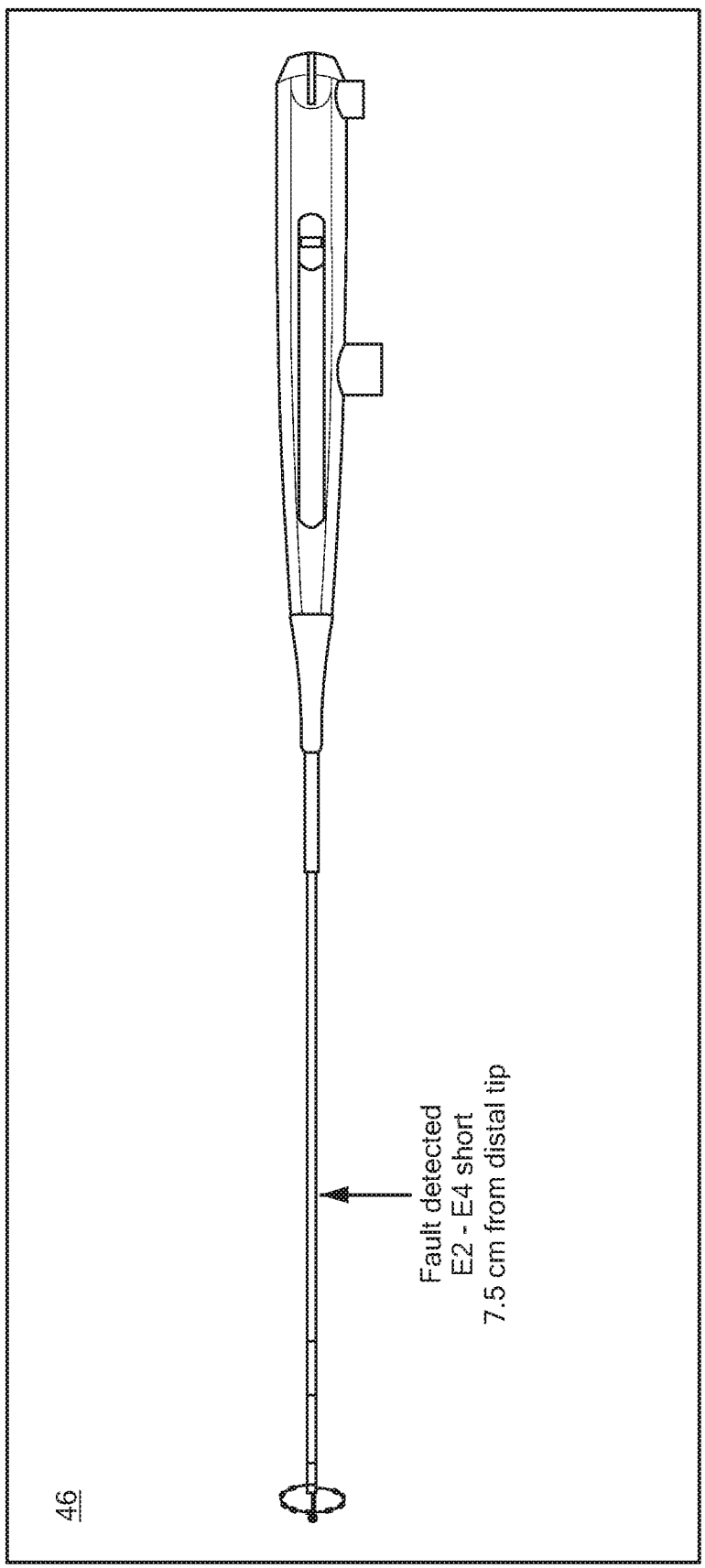
FIG. 15 shows an exemplary informational display in which information is presented relative to an image of a device.

Non-limiting examples of informational displays are shown in FIGS. 13-15. In FIGS. 13 and 14, information about a fault is shown in a matrix that indicates which, if any, wires are damaged. In FIG. 15, information about a fault is shown relative to an image of the device, which tells the user where the fault is located within the device. Both formats may quickly and clearly communicate a fault condition to the user so the delivery of energy to the patient may be terminated or modified as soon as possible.

Figure 16:
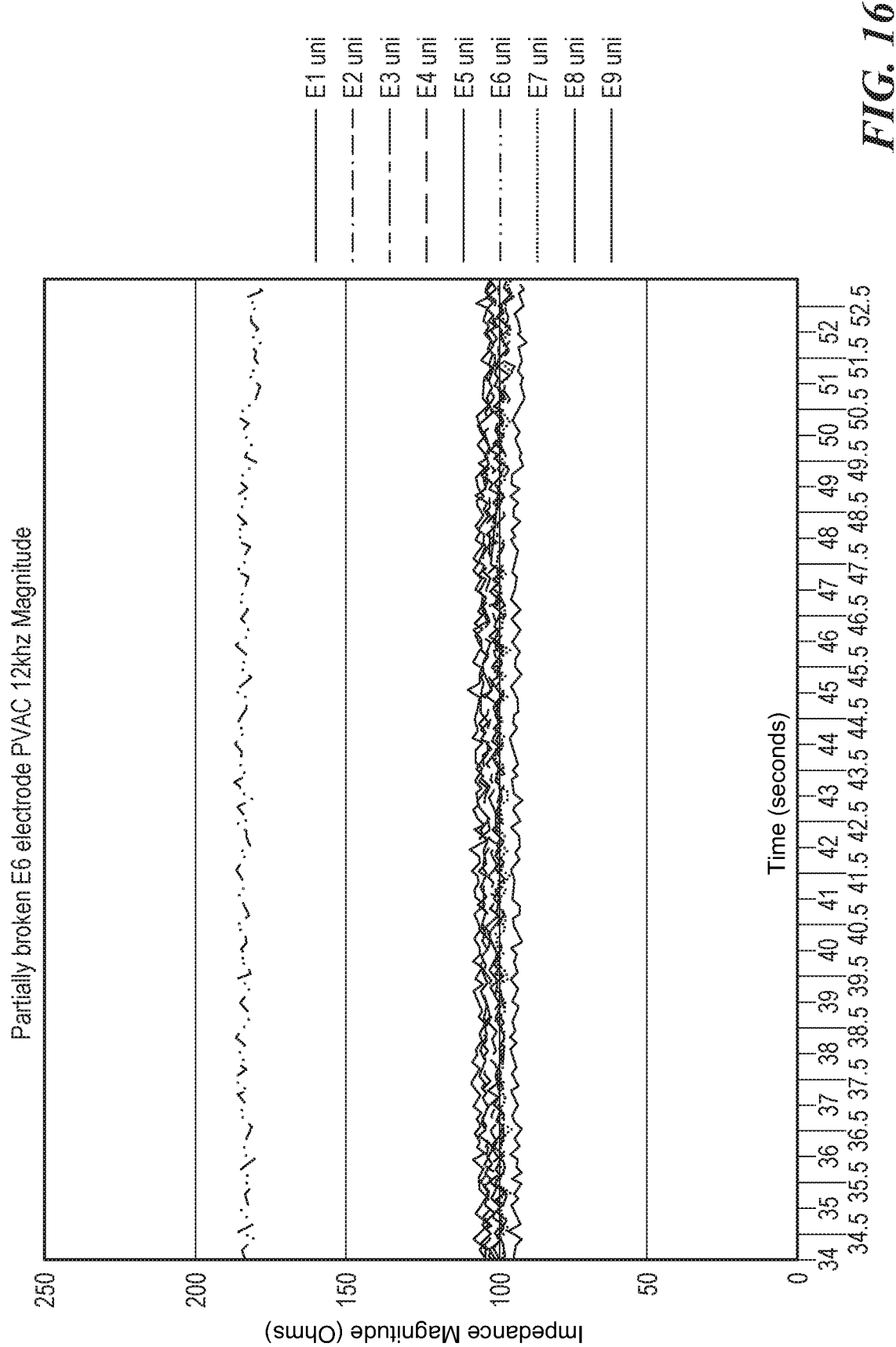
FIGS. 16 and 17 show exemplary informational displays in which information is presented in a graph.
Figure 17:
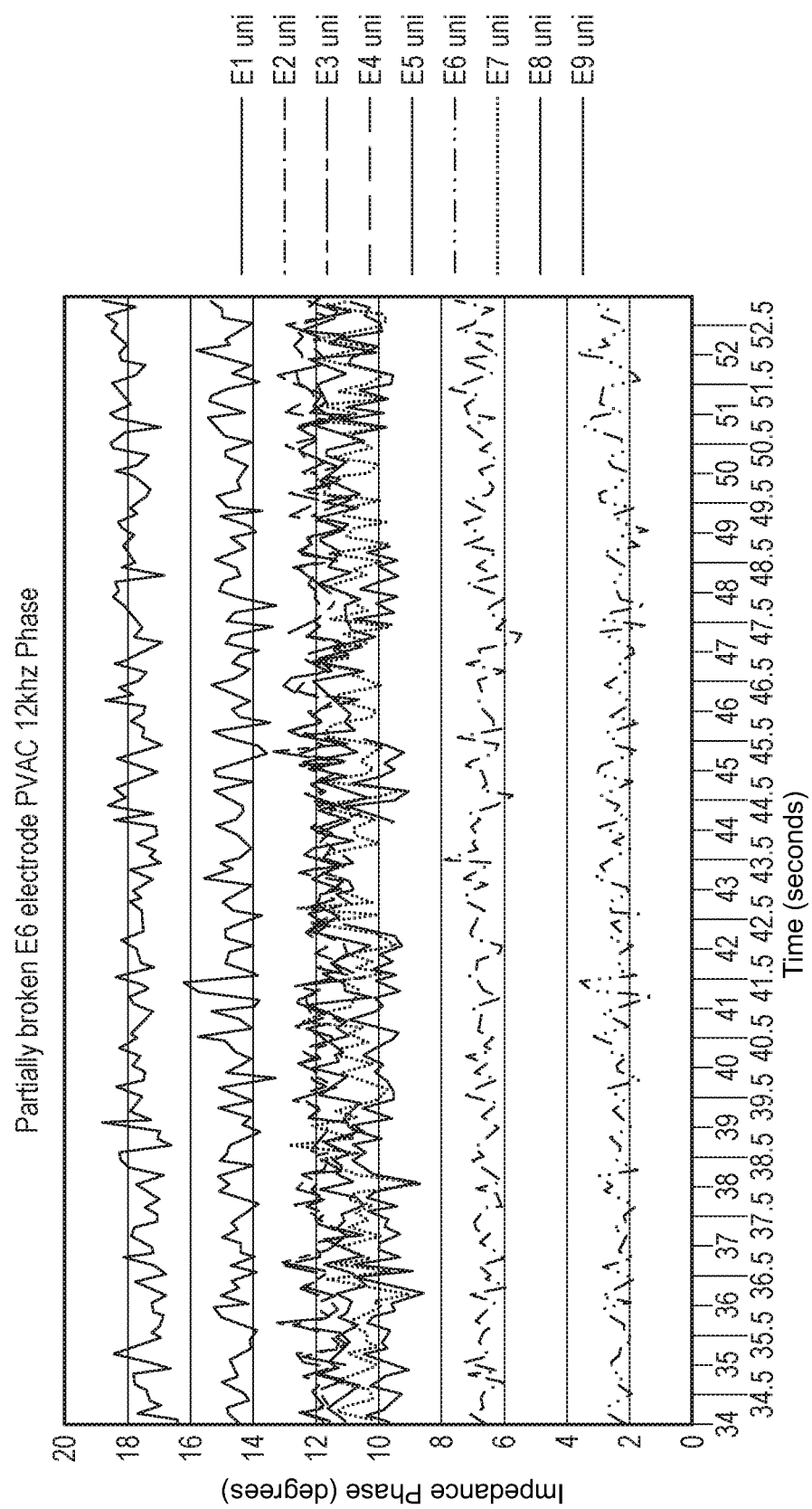

Exemplary data is shown in FIGS. 16 and 17, which illustrate impedance measurement values (both magnitude and phase components) for an electrode, electrode E6, that shows signs of becoming compromised. As shown in FIG. 16, magnitude measurements over time for faulty electrode E6 are greater than magnitude measurements over time of the other electrodes (in this example, electrodes E1-E6 and electrodes E7-E9). Conversely, as shown in FIG. 17, phase measurements over time for faulty electrode E6 are lower than phase measurement values for the other electrodes (in this example, electrodes E1-E6 and electrodes E7-E9).

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. A method of determining a fault location within a medical system, the method comprising:
 providing a medical device;
 applying a first complex current at first frequency and a second complex current at a second frequency;
 measuring a first total complex impedance at the first frequency;
 measuring a second total complex impedance at the second frequency;
 determining a wire impedance within the medical device by
  calculating a first blood impedance based on the first total complex impedance at the first frequency during delivery of the first complex current while the medical device is in contact with a target tissue,
  calculating a second blood impedance based on the second total complex impedance at the second frequency during delivery of the second complex current while the medical device is in contact with the target tissue, and
  calculating a first complex wire impedance within the medical device based on the first blood impedance and calculating a second complex wire impedance within the medical device based on the second blood impedance;
 determining a real component and an imaginary component of the first complex wire impedance;
 determining a real component and an imaginary component of the second complex wire impedance;
 comparing the real component and the imaginary component of each of the first and second complex wire impedances to a set of reference real components and a set of reference imaginary components, wherein the set of reference real components and the set of reference imaginary components each indicate a reference real component and a reference imaginary component for each of a plurality of fault locations; and determining a distance of the fault location from a proximal end of the medical device based on the comparison.

2. The method of claim 1, wherein the set of reference real components and the set of reference imaginary components each further indicate a reference real component for each of the plurality of fault locations for a first fault type, a reference imaginary component for each of the plurality of fault locations for the first fault type, a reference real component for each of the plurality of fault locations for a second fault type, and a reference imaginary component for each of the plurality of fault locations for the second fault type, the method further comprising determining whether the fault is the first fault type or the second fault type based on the comparison.

3. The method of claim 1, wherein the medical device further includes at least two electrode wires and at least one electrode, the at least one electrode and at least two electrode wires being electrically coupled, a second complex impedance at a second frequency being configured to measure the electrical coupling of the at least one electrode and at least a first electrode wire and a second electrode wire of the at least two electrode wires.

4. The method of claim 3, wherein the at least two electrode wires includes a first electrode wire having a known resistance and a series impedance and a second electrode wire having a known resistance and a series impedance.

5. The method of claim 4, wherein the first electrode wire is composed of at least one of a group consisting of a copper and a copper alloy and the second electrode wire is composed of constantan.

6. The method of claim 4, wherein the first electrode wire is composed of a copper.

7. A system for determining a location within a medical device of a fault in an energy delivery pathway, the system comprising:

an energy generator including a processing unit, the energy generator being configured to:
deliver a first complex current at a first frequency and a second complex current at a second frequency,
during delivery of the first complex current, calculate a first blood impedance at the first frequency when the medical device is in contact with a target tissue,
during delivery of the second complex current, calculate a second blood impedance at the second frequency when the medical device is in contact with the target tissue, and
calculate a wire impedance within the medical device based on the first blood impedance and the second blood impedance;

an electrode distribution system including a processing unit and a complex impedance measuring device, the electrode distribution system being in communication with the energy generator, the complex impedance measuring device having a radiofrequency generator and being configured to render a real portion and an imaginary portion of an impedance measurement;

the medical device in communication with the electrode distribution system including an elongate body having a proximal portion, a distal portion, and a lumen extending between the proximal portion and the distal portion, a treatment element at the distal portion having at least one electrode, and at least one electrode wire, each of the at least one electrode being connected to one of the at least one electrode wire, the energy delivery pathway including at least a part of each of the at least one electrode wire and having a forward portion and a rearward portion, the radiofrequency generator of the complex impedance measuring device being configured to deliver a first test signal along each of the forward portion and the rearward portion of the energy delivery pathway at a first frequency and a second test signal along each of the forward portion and the rearward portion of the energy delivery pathway at a second frequency, the processing unit and complex impedance measuring device being configured to:
calculate a first complex wire impedance rendered at the first frequency at a known reference point inside the electrode distribution system based on incident and reflected waves in each of the forward and rearward portions of the energy delivery pathway;
calculate a second complex wire impedance rendered at the second frequency at the known reference point inside the electrode distribution system based on incident and reflected waves in each of the forward and rearward portions of the energy delivery pathway; and
identify a location of a fault in the energy delivery pathway within the system by comparing the real and imaginary components of each of the first and second complex wire impedances rendered by the impedance measuring device to a set of reference real components and a set of reference imaginary components.

8. The system of claim 7, wherein the first frequency is approximately 100 MHz and the second frequency is approximately 65 MHz.

9. The system of claim 7, wherein the impedance measuring device is configured to identify the location of the fault in the energy delivery pathway by:
comparing the real and imaginary components of the first complex wire impedance to threshold real and imaginary components; and
comparing the real and imaginary components of the second complex wire impedance to the threshold real and imaginary components.

10. The system of claim 9, wherein the impedance measuring device is further configured to minimize the root sum square error between the threshold real and imaginary components, the real and imaginary components of the first complex wire impedance, and the real and imaginary components of the second complex wire impedance.

11. The system of claim 9, wherein the threshold real and imaginary components include:
a threshold real component for a first fault type;
a threshold real component for a second fault type;
a threshold imaginary component for the first fault type; and
a threshold imaginary component for the second fault type.

12. The system of claim 11, wherein the threshold real and imaginary components are stored in the processing unit as a look-up table.

13. The system of claim 7, wherein the treatment element further includes: a carrier element; and
the at least one electrode is coupled to the carrier element.

14. The system of claim 13, wherein the carrier element is transitionable between a first linear configuration and a second expanded configuration.

15. The system of claim 14, wherein the carrier element is arcuate in the expanded configuration.

16. The system of claim 14, wherein the carrier element is substantially circular in the expanded configuration.

17. The system of claim 7, wherein:
the energy generator is further configured to deliver ablation energy to the at least one electrode; and
the processing unit is further configured to prevent delivery of the ablation energy to at least one of the at least one electrode when the processing unit determines a fault in the energy delivery pathway exists.

18. The system of claim 7, wherein the energy generator includes a first voltage source having a known voltage and a second voltage source having a known voltage.

19. The system of claim 18, wherein the at least one electrode wires includes:
a first electrode wire having a known resistance and series impedance; and
a second electrode wire having a known resistance and a series impedance.

20. A method of determining a fault location within a medical system, the method comprising:
providing a medical device, the medical device having:
a proximal end; and
a distal end opposite the proximal end;
applying a first complex current;
applying a second complex current different than the first complex current;
measuring a first total complex impedance at the first frequency;
measuring a second total complex impedance at the second frequency;
during delivery of the first complex current, calculate a first blood impedance based on the first total complex impedance when the medical device is in contact with a target tissue;
during delivery of the second complex current, calculate a second blood impedance based on the second total complex impedance when the medical device is in contact with the target tissue;
calculating a first complex wire impedance within the medical device based on the first blood impedance and a second complex wire impedance within the medical device based on the second blood impedance; and
determining a distance of the fault location from the proximal end of the medical device by comparing a real component of the first complex wire impedance, an imaginary component of the first complex wire impedance, a real component of the second complex wire impedance, and an imaginary component of the second complex wire impedance to a set of reference real components and a set of reference imaginary components.

* * * * *